(12) United States Patent
Concin et al.

(10) Patent No.: US 12,011,019 B2
(45) Date of Patent: *Jun. 18, 2024

(54) METHOD AND DEVICE FOR TREATING FOOD AND/OR CONTAINERS FOR HOLDING FOOD

(71) Applicant: Red Bull GmbH, Fuschl am See (AT)

(72) Inventors: Roland Concin, Fuschl am See (AT); Harald Eder, Eugendorf (AT); Christian Rinderer, Fuschl am See (AT); Matthias Rinderer, Fuschl am See (AT); Volker Viechtbauer, Fuschl am See (AT)

(73) Assignee: Red Bull GmbH, Fuschl am See (AT)

( * ) Notice: Subject to any disclaimer, the term of this patent is extended or adjusted under 35 U.S.C. 154(b) by 54 days.

This patent is subject to a terminal disclaimer.

(21) Appl. No.: 15/538,315

(22) PCT Filed: Dec. 22, 2015

(86) PCT No.: PCT/AT2015/050326
§ 371 (c)(1),
(2) Date: Aug. 10, 2017

(87) PCT Pub. No.: WO2016/100996
PCT Pub. Date: Jun. 30, 2016

(65) Prior Publication Data
US 2017/0360068 A1    Dec. 21, 2017

(30) Foreign Application Priority Data

Dec. 22, 2014  (AT) .............................. A 50935/2014

(51) Int. Cl.
*A23L 3/00*    (2006.01)
*A23L 2/46*    (2006.01)
(Continued)

(52) U.S. Cl.
CPC ................ *A23L 3/001* (2013.01); *A23L 2/46* (2013.01); *A23L 3/00* (2013.01); *A23L 3/02* (2013.01);
(Continued)

(58) Field of Classification Search
CPC ....... Y02A 40/965; B65B 55/02; B65B 55/04; B65B 55/06; B65B 55/10; A23L 3/02;
(Continued)

(56) References Cited

U.S. PATENT DOCUMENTS 2,025,990 A † 12/1935 Kokemper
2,282,187 A †  5/1942 Herold
(Continued)

FOREIGN PATENT DOCUMENTS

AU    2011379616    †  5/2013
CN    2017 18422 U       1/2011
(Continued)

OTHER PUBLICATIONS

DE 102007003919 Espacenet Translation.*
(Continued)

*Primary Examiner* — Viren A Thakur
*Assistant Examiner* — Ashley Axtell
(74) *Attorney, Agent, or Firm* — Collard & Roe, P.C.

(57) ABSTRACT

A method and a device for treating food and/or containers for holding food treats the food and/or containers in at least one treatment zone by a process liquid, wherein the process liquid is at least partially recirculated into the treatment zone or the treatment zones after completed treatment of the food and/or the containers. During continuous treatment at least some or all of the process liquid is used per time unit to form at least one stream of the process liquid, the formed stream is filtered by at least one membrane filtration system, and a filtered stream is at least partially fed back into an element (Continued)

holding and/or conducting the process liquid and/or into a treatment zone.

18 Claims, 6 Drawing Sheets

(51) Int. Cl.

| | | |
|---|---|---|
| A23L 3/02 | (2006.01) | |
| A23L 3/18 | (2006.01) | |
| A23L 3/28 | (2006.01) | |
| A61L 2/02 | (2006.01) | |
| A61L 2/10 | (2006.01) | |
| A61L 9/00 | (2006.01) | |
| B65B 55/02 | (2006.01) | |
| C02F 1/32 | (2023.01) | |
| C02F 1/44 | (2023.01) | |
| C02F 9/00 | (2023.01) | |
| C12H 1/16 | (2006.01) | |
| C02F 1/02 | (2023.01) | |
| C02F 1/28 | (2023.01) | |
| C02F 103/02 | (2006.01) | |

(52) U.S. Cl.
CPC ............... *A23L 3/18* (2013.01); *A23L 3/28* (2013.01); *A61L 2/02* (2013.01); *A61L 2/10* (2013.01); *A61L 9/00* (2013.01); *B65B 55/025* (2013.01); *C02F 1/32* (2013.01); *C02F 1/444* (2013.01); *C02F 9/00* (2013.01); *C12H 1/16* (2013.01); *A61L 2202/23* (2013.01); *C02F 1/02* (2013.01); *C02F 1/28* (2013.01); *C02F 2103/02* (2013.01); *C02F 2209/001* (2013.01); *C02F 2209/003* (2013.01); *C02F 2209/02* (2013.01); *C02F 2209/11* (2013.01)

(58) Field of Classification Search
CPC ........ A23L 3/00–14; A61L 2/02; A61L 2/022; A61L 2203/23
USPC ................................ 426/407; 53/426, 425
See application file for complete search history.

(56) References Cited

U.S. PATENT DOCUMENTS

| | | | |
|---|---|---|---|
| 2,581,125 A † | 1/1952 | Morrison | |
| 3,151,540 A * | 10/1964 | Der Winden | A23L 3/001 |
| | | | 99/360 |
| 4,396,582 A | 8/1983 | Kodera | |
| 4,571,301 A * | 2/1986 | Inskeep, Jr. | C02F 1/00 |
| | | | 210/304 |
| 4,704,958 A * | 11/1987 | Braymand | A23L 3/04 |
| | | | 99/470 |
| 5,057,229 A * | 10/1991 | Schulenburg | C02F 1/008 |
| | | | 210/139 |
| 5,173,190 A * | 12/1992 | Picek | B01D 17/02 |
| | | | 210/259 |
| 6,186,193 B1 | 2/2001 | Phallen et al. | |
| 6,540,922 B1 | 4/2003 | Cordemans et al. | |
| 8,518,269 B2 † | 8/2013 | Fischmann T. | |
| 2003/0205514 A1 | 11/2003 | Potter et al. | |
| 2006/0257544 A1 † | 11/2006 | Edens | |
| 2007/0181496 A1 * | 8/2007 | Zuback | B01D 61/025 |
| | | | 210/636 |
| 2007/0272877 A1 | 11/2007 | Tribelsky et al. | |
| 2008/0044533 A1 | 2/2008 | Nagaoka et al. | |
| 2009/0000639 A1 | 1/2009 | Tribelsky et al. | |
| 2009/0280222 A1 * | 11/2009 | Nielsen | A23L 3/003 |
| | | | 426/232 |
| 2009/0324790 A1 | 12/2009 | Hilgren et al. | |
| 2010/0162662 A1 * | 7/2010 | Iwashita | B67C 7/0073 |
| | | | 53/426 |
| 2010/0178201 A1 | 7/2010 | Tribelsky et al. | |
| 2012/0006817 A1 | 1/2012 | Runge | |
| 2012/0070540 A1 | 3/2012 | Igarashi | |
| 2014/0110360 A1 * | 4/2014 | Braun | B01D 35/02 |
| | | | 210/805 |
| 2015/0166361 A1 * | 6/2015 | Fischmann | C02F 1/52 |
| | | | 210/709 |
| 2015/0368135 A1 † | 12/2015 | Muenzer | |
| 2017/0360069 A1 | 12/2017 | Concin et al. | |

FOREIGN PATENT DOCUMENTS

| | | | |
|---|---|---|---|
| DE | 296 16 876 U1 | 1/1997 | |
| DE | 102007003919 A1 * | 7/2008 | ............... A23L 2/46 |
| EP | 2261169 † | 12/2010 | |
| EP | 1 654 006 B1 | 1/2014 | |
| EP | 2 722 089 A1 | 4/2014 | |
| EP | 2 959 782 A2 | 12/2015 | |
| JP | 108-019386 A | 1/1996 | |
| JP | H08-322528 A | 12/1996 | |
| JP | H11-105830 A | 4/1999 | |
| JP | 2000-246206 A | 9/2000 | |
| JP | 2005-021864 A | 1/2005 | |
| JP | 2005-034694 A | 2/2005 | |
| JP | 2005-137949 A | 6/2005 | |
| JP | 2005-296414 A | 10/2005 | |
| JP | 2005-319405 A | 11/2005 | |
| JP | 2006-109752 A | 4/2006 | |
| JP | 2007-501693 A | 2/2007 | |
| JP | 3 922 935 B2 | 5/2007 | |
| JP | 2014-128802 A | 7/2014 | |
| JP | 2018-508420 A | 3/2018 | |
| WO | 94/19968 † | 9/1994 | |
| WO | 2004/082406 A1 | 9/2004 | |
| WO | 2005/011754 A1 | 2/2005 | |
| WO | 2008136741 A1 | 11/2008 | |
| WO | 2009/156972 A2 | 12/2009 | |
| WO | 2011/131963 † | 10/2011 | |

OTHER PUBLICATIONS

Fahnrich et al. USPTO Translation.*
Faehnrich A et al: "Aufbereitung von schwach belasteten Prozesswaessern in der Lebensmittelindustrie", Chemie Ingenieur Technik (69) 8197, Aug. 1, 1997, pp. 1147-1148, with English extract.
Third Party Submission under 37 CFR 1.290 Concise Description of Relevance in U.S. Appl. No. 15/538,405, (filed Jun. 6, 2019).
International Search Report of PCT/AT2015/050326, mailed May 2, 2016.
International Search Report of PCT/AT2015/050327, mailed Apr. 28, 2016.
Faehnrich A et al: "Aufbereitung von schwach belasteten Prozesswaessern in der Lebensmittelindustrie", Chemie Ingenieur Technik (69) 8197, Aug. 1, 1997, pp. 1147-1148.
English translation of Japanese Search Report dated Aug. 23, 2019 in Japanese Application No. 2017-533888.
English translation of Notice of Reasons for Refusal dated Sep. 3, 2019 in Japanese Application No. 2017-533888.
English translation of Japanese Search Report dated Jul. 12, 2019 in Japanese Application No. 2017-533869.
English translation of Notice of Reasons for Refusal dated Jul. 23, 2019 in Japanese Application No. 2017-533869.
The wastewater collection processing and the industrial machine using the NF membrane in a beverage production factory, Japan Society of Industrial Machinery Manufacturers, 2003, No. 635, pp. 66-68, Masazumi Oba, etc. (relevance set forth in Jul. 12, 2019 Japanese Search Report in Japanese Application No. 2017-533869—category A).

\* cited by examiner
† cited by third party

METHOD AND DEVICE FOR TREATING FOOD AND/OR CONTAINERS FOR HOLDING FOOD

CROSS REFERENCE TO RELATED APPLICATIONS

This application is the National Stage of PCT/AT2015/050326 filed on Dec. 22, 2015, which claims priority under 35 U. S. C. § 119 of Austrian Application No. A 50935/2014 filed on Dec. 22, 2014, the disclosure of which is incorporated by reference. The international application under PCT article 21 (2) was not published in English.

BACKGROUND OF THE INVENTION

1. Field of the Invention

The invention relates to a method for treating food and/or containers for holding food and to a device for treating food and/or containers for holding food. In particular, the invention relates to a method and device for treating luxury food, especially alcoholic and non-alcoholic drinks. The food, in particular the luxury food, and the containers for holding the food are treated with a process liquid in at least one treatment zone. According to the invention, during treatment at least some or all of the at least partially recirculated process liquid is used to form at least one stream of the process liquid and filtered using a membrane filtration system.

2. Description of the Related Art

Various variations of methods and devices for treating products and/or containers are known from the prior art. Often the products, for example foodstuffs, and/or the containers are treated by a tempered process liquid, as is e.g. the case in pasteurization of food products in so-called pasteurizers. In most cases, water or an aqueous solution is used as the process liquid and acts indirectly on the products or directly on the containers.

To avoid creating large quantities of liquid waste and waste water, the process liquid or process water is often at least partially circulated through the device or the treatment zone(s), i.e. the process liquid is re-used in a circulation procedure. However, this procedure entails a high potential for dirtying and contamination of the process liquid. Systems for treating products or containers are usually accessible, the conditions by no means consist of controlled air circulation or the like. There are other sources of dirt in addition to the ambient air, for example the operating staff or other people, conveying elements for the containers and products, any cooling equipment for the process liquid, especially air-conditioned cooling towers, or even the process liquid freshly introduced into the method or device itself. Furthermore, contaminants can enter through the treatment process itself, such as through damage to the containers and contaminants in the process liquid caused by the product or through the detaching of particles such as paint particles or the like from the outside of the containers.

In the past a number of methods have been suggested for removing contaminants from a process liquid. These consist of filtration measures for removal of relatively coarse or large particles, such as glass shards, sand, gravel, and the like. An example is EP 2 722 089 A1. EP 2 722 089 A1 describes a device for thermal treatment of products in containers. The containers are sprinkled or sprayed with a process liquid and the process liquid, e.g. water, is recirculated for at least partial re-use. A gravitational sedimentation device is used to clean the process liquid that can separate out coarse-grained or large particles like glass shards or sand.

The methods known from the prior art describe filtration methods for separating relatively large particles out of a process liquid using separating devices such as conventional mesh sieves, filter bands, or detachable sieves, or in fact sedimentation devices.

However, the measures known from the prior art are not suitable for removing in particular impurities with relatively small particle sizes from the process liquid. This especially affects particle contaminants that cannot be removed by conventional filter sieves and other separating devices, or e.g. do not or only very slowly precipitate out of a process water stream.

In particular, in devices for thermal treatment of products and containers with a process liquid or process water, micro-organisms can reproduce in the process water to a considerable extent over time. Such micro-organisms, for example bacteria, fungal spores, but also viruses, can be introduced into the device by fresh process water but also by operating staff or other persons. Ultimately the formation and growth of e.g. algae may follow. In thermal treatment, the process water often has temperatures in at least some zones that even favor the growth and reproduction of micro-organisms. In general, it cannot be wholly ruled out that e.g. bacterial cultures may get on the outside of the containers in the course of the treatment and at least partially remain there even after the treatment process.

Particularly problematic in regard to filtration by conventional sieves is the disadvantageous distribution of particle sizes in a typical process water. In particular, the use of chemicals like surfactants favors very small particle sizes that cannot be removed from the process liquid by conventional separating devices or only to an inadequate extent. For this reason, production and treatment in currently known methods for treating products and containers in which the process liquid is at least partially recirculated must be interrupted at relatively short intervals to clean and sterilize the treatment device. Such cleaning processes are typically very laborious and in particular lead to production losses and as a consequence to financial losses.

SUMMARY OF THE INVENTION

It is therefore the aim of the invention to develop an improved method and an improved device that can eliminate the deficits still existing in the prior art. In particular, in comparison to the prior art an improved method and improved device for treating products, especially food products, and/or containers is to be provided, in which method or device the process liquid can be at least partially recirculated for re-use in the method, but the disadvantages associated with this due to continuously increasing dirtying or contamination of the process liquid are avoided as much as possible.

The aim of the invention is achieved by providing a method for treating food and containers for holding food using a process liquid in at least one treatment zone, in which method at least one membrane filtration system is provided for continuous cleaning of some or all of the process liquid.

The food and the containers are introduced into a treatment zone or conveyed through a treatment zone. At least one liquid stream of the process liquid is conducted into the treatment zone or treatment zones to act on the food or containers, and discharged from the treatment zone again after completed treatment of the food products and containers, wherein the process liquid for treating the food and containers is at least partially recirculated into the treatment zone or the treatment zones for the purpose of re-use in the method.

In particular, in the continuous, ongoing treatment, at least some or all of the process liquid out of the total process liquid conducted through all existing treatment zones per time unit is used or taken in each time unit to form at least one stream of the process liquid, and the at least one resulting stream of the process liquid is filtered by at least one membrane filtration system in order to clean and sterilize the process liquid, especially to remove particles from the process liquid, and after the filtration process an irradiated and/or filtered stream is at least partially returned to an element holding or conducting the process liquid and/or to a treatment zone.

Here and below, an element holding or conducting the process liquid or a conduction element for the process liquid means any element that is designed to hold the process liquid or to conduct a liquid stream of the process liquid. These can be, for example, piping, ducts, and the like in which the process liquid is e.g. fed into a treatment zone or discharged from a treatment zone. The term "conduction element" further means, for example but not exclusively reservoirs, tanks, or collection devices for the process liquid arranged inside or outside the treatment zones or the like.

Here and below, a treatment zone means a zone in which the food is brought into contact with the process liquid, preferably indirectly, and/or the containers are brought into contact with the process liquid, preferably directly. The physical and/or chemical and/or other parameters of the process liquid can be adjusted specifically for the relevant treatment purpose. The process liquid can affect the food and the containers for holding food in various ways. For example, to generate the desired interaction the process liquid and a liquid foodstuff to be treated can be conducted in a materially separated manner in a counter current, direct current, or cross flow arrangement in adjacent conduction elements. The desired interaction can be achieved by heat transfer between the food and the process liquid in the sense of a heat exchanger, as for example is usual in the pasteurization of milk for preservation. Another frequently used method is the pasteurization of food products in which the food is already in a closed container and the process liquid acts on the outside of the containers. The process liquid can be poured on the outside of the containers or the containers can be sprinkled or sprayed with the process liquid. In another example, dipping methods are also possible in which containers holding food are dipped into the process liquid. Naturally, however, the invented method and invented device can also be used for treatment, e.g. rinsing/cleaning of empty containers. Finally, the term treatment zone means, at least in the broadest sense, also an element holding or conducting the process liquid or a conduction element for the process liquid.

Here and below, a liquid stream of the process liquid means any kind of conducted movement of the process liquid, regardless of how the liquid stream or its conduction are designed. This means that the term "liquid stream" comprises, for example, a stream of a moved process liquid in conduction elements like piping, ducts, reservoirs, tanks, etc. just as much as, for example, a sprinkling or spray stream of the process liquid free falling under ambient air pressure in a treatment zone or a stream of the process liquid in a retooling apparatus or the like.

Through the measures according to the invention, a method can be prepared that is eminently suitable especially for the removal of impurities or contaminants with a very small particle size such as bacteria colonies from the process liquid and for sterilizing the process liquid. This allows a significant improvement to be achieved compared to known methods, which are of only limited or even of no use in removing small particles as well as micro-organisms from an at least partially recirculated process liquid. In this way, contamination of the process liquid conducted through all existing treatment zones can be effectively impeded. Advantageously, the microfiltration or ultrafiltration by the membrane filtration system(s) can be performed during ongoing operation and is comparatively efficient and energy-saving.

The exact number, type, and location of integration of the membrane filtration system(s) and the connection of a membrane filtration system to the conduction elements conducting the process liquid and/or treatment zone(s) can be determined or implemented in due consideration of structural features, process parameters, and the like. However, specific arrangement variations can offer advantages for the method for treating food and containers, which will be explained in more detail below.

For example, additional dirt traps or the like can be arranged in the conduction elements to filter out large-grained impurities in the process liquid. For example, a gravitational sedimentation device as described in the previously cited EP 2 722 089 A1 can be used to separate large or large-grained particles.

The measures according to the invention also succeed in reducing as much as possible laborious and expensive interruptions in the production or treatment in order to clean and sterilize the treatment device or at least in significantly lengthening the time intervals between such cleaning processes. In addition, the membrane filtration can at least reduce the quantity of chemical stabilizers used to prepare the process liquid, especially the required quantities of surfactants, corrosion inhibitors, and/or disinfectants, and the use of cleaning chemicals can be at least largely avoided or minimized.

The continuous removal of contaminants, especially particles of micro-organisms such as bacteria colonies, can additionally at least strongly reduce the use of biocides. Therefore and in addition, a significant improvement in environmental stress can be achieved and the burden on a facility, such as a purification plant, placed after the method or device can be minimized.

The invented measures can also improve olfactory factors as the formation of undesirable or unpleasant smells can be hindered. Various micro-organisms, especially bacteria, are known for generating bad smells as products of their metabolism. The removal of these micro-organisms from the process liquid can largely prevent unpleasant smells.

If bacterial cultures remain in a process liquid for a longer time under simultaneous use of biocides, bacterial strains can "get used to" the biocides being used or bacterial strains resistant to the biocides being used can be formed. This means that biocides can become ineffective at removing micro-organisms from the process liquid over time. Through continuous removal of the micro-organisms from the process liquid by microfiltration by at least one membrane filtration system, the formation of resistant germs can be hindered as much as possible and the use of biocides can be minimized overall as an efficient and effective means is provided to in general continuously remove micro-organisms of all kinds from the process liquid. Through filtration using at least one membrane filtration system, e.g. biocide-resistant and/or chlorine-resistant bacterial strains can be effectively removed from the process liquid.

Naturally other organic and inorganic small and microparticles can also be removed from the process liquid by the at least one membrane filtration system. This simultaneously results in further improvement in regard to micro-organism growth and to the growth rate of micro-organisms in the process liquid, as organic and inorganic small and microparticles can often act as good nutritional bases or "breeding grounds," e.g. for bacteria. The removal of unwanted particle contaminants using membrane filtration can significantly reduce the use of otherwise necessary chemicals for elimination of such contaminants, such as surfactants.

The invented measures can also remove dust-like impurities from the process liquid. Such impurities can, for example, be caused in the course of manufacturing the containers by shaping or cutting process steps like cutting, milling, drilling or the like. The manufacturing of containers can cause e.g. glass of metal dust, especially aluminum dust, which dust can be introduced into the method for treating food and containers along with the containers.

Finally, the invented measures can effectively hinder dirtying of the outside of the containers as well as dirtying of the surfaces of the device for treating the food and containers by the process liquid itself. This brings further advantages in regard to any secondary treatment or additional cleaning actions, whose extent can at least be reduced. Where appropriate, the invented measures can make secondary cleaning of the containers with washing chemicals and/or sterilization of the containers superfluous.

The additional measure of filling the products or food to be treated into containers before the treatment, closing the containers, and applying the process liquid to the outside of the containers in such a way that the process liquid flows around the outside of the containers represents a particularly efficient measure for treating food, since an already filled trade product can be put out after the treatment. In addition, this way the risk of recontamination of the food during a filling step following the treatment can be ruled out.

By setting the temperature of the process liquid before treatment of the food and executing the treatment of the food through indirect heat transfer using the process liquid, direct contact between the food and heating and/or cooling means or the process liquid can be avoided. Furthermore, this characteristic of the method is an effective means for setting a treatment temperature for the food and the food can be treated particularly efficiently in this way It can further be advisable to pasteurize the food in at least one treatment zone using heated process liquid. This can achieve a longer shelf life for the food.

Setting the temperatures of the liquid streams of the process liquid separately in a controlled manner before feeding them into a treatment zone has the advantage that the overall procedure for treating the food or containers is easier to control. In particular, this can prevent unwanted damage to the food and/or containers because of overly quick or high temperature changes.

It can be useful especially in regard to pasteurization of food to successively heat up the food being treated, especially luxury food products, in at least one treatment zone, to pasteurize them in at least one treatment zone, and to cool them in at least one treatment. On the one hand, slow heating in at least one heating zone can guarantee gentle heating of the food. On the other hand, active cooling in at least one cooling zone after pasteurization can effectively prevent so-called "over-pasteurization" because of food being at a high temperature for too long of a time. Such over-pasteurization often caused unwanted changes in the food and can negatively influence the flavor and/or smell of the food. The disclosed process steps for sequential treatment of foodstuffs, especially luxury food products, allows well-controlled and gentle process guidance for the foodstuffs. For example, the temperature of the process liquid can be increased step by step from room temperature to, for example, 65° C. for multiple heating zones, in one or more zones the process liquid can be introduced at a pasteurizing temperature such as 80 to 85° C. and then the process liquid can be introduced into multiple cooling zones for the foodstuffs or containers, again in the form of zones, with sequentially lower temperatures for cooling the feeds food or containers.

Alternatively to the stated temperature ranges, which are given as examples for the pasteurization of food, other temperature ranges can of course also be advisable for other treatment processes. Another example given at this juncture is superheated steam sterilization, in which the process liquid or process water reaches temperatures above 100° C. such that at least in the sterilization zones process water acts on the containers in a gaseous state.

It has proven particularly practical if a liquid stream is fed into at least one treatment zone for heating the food and/or the containers at a temperature between 40° C. and 50° C. This provides particularly gentle pre-heating of the food and allows large temperature differences or temperature jumps to be avoided in the course of pre-heating the food or the containers.

In regard to cleaning efficiency for the process liquid during continuous treatment, it can be advisable to select the process liquid quantities used to form at least one stream of the process liquid out of at least one element holding and/or conducting the process liquid during continuous treatment per time unit in such a way that the filtration of the stream or streams allow a removal rate for micro-organisms to be achieved that is larger than the growth rate of these micro-organisms in the process liquid in the same time interval. This in particular allows the total quantity of micro-organisms in the process liquid to be minimized as much as possible and an increase in the total quantity of micro-organisms in the process liquid during continuous treatment of the food and/or containers to be effectively prevented.

Surprisingly, it has been shown that filtration of a relatively small partial quantity of the process liquid per time unit out of the total liquid streams of the process liquid conducted through the device or treatment zones per time unit is entirely sufficient to achieve an adequate filtration result and to obtain a process liquid with adequate purity. This way the size and/or the number of membrane filtration system(s) can be kept comparatively small without having to compromise on the purity of the process liquid. In addition, the amount of energy used to clean the process liquid can be further reduced.

It can also be useful to select or set the quantity of process liquid used to form at least one stream of the process liquid to be filtered out of at least one element containing or conducting the process liquid per time unit in such a way that—based on the total process liquid conducted through all existing treatment zones per time unit—at least 1% and less than 25% per time unit is used to form at least one stream of the process liquid and this partial quantity of the process liquid formed per time unit is filtered by at least one membrane filtration system. This can ensure on the one hand that a sufficiently high number of impurities, especially small particles, are removed from the process liquid during ongoing treatment. On the other hand, this can also avoid overly laborious structural design of a membrane filtration system or the use of a large number of membrane filtration systems. Finally, this percentage range for filtered quantities of process liquid per time unit gives a range within which a reasonable adjustment of various process directions and process aims can be undertaken, especially the initial quality of the process liquid and the contamination rate existing in the treatment method itself. It is preferable to set the quantity of process liquid used to form at least one stream of the process liquid to be filtered out of at least one element containing or conducting the process liquid per time unit in such a way that—based on the total process liquid conducted through all existing treatment zones per time unit—between 2% and 10%, and especially between 2.5% and 7% per time unit is used to form at least one stream of the process liquid and this partial quantity of the process liquid formed per time unit is filtered by at least one membrane filtration system.

It can also be useful if during continuous treatment the total volume of process liquid contained in the device for treating food or containers is conducted through one or more membrane filtration system(s) and filtered at least 1 time and preferably between 2 times and 10 times per day. This way it can again be ensured that depending on various process parameters, for example on the initial quality of the process liquid, on the contamination rate in the treatment method itself, and especially on the micro-organism growth rate in the process liquid, a sufficient quantity of the process liquid can be cleaned by forming at least one stream and filtering the formed stream or the formed streams using at least one membrane filtration system.

In principle, a membrane filtration system can be connected in series on the inlet side to an element holding or conducting the process liquid, such as piping. In this case, the entire liquid stream of the process liquid flowing through this conduction element or piping is conducted through the membrane filtration system and filtered.

Alternatively, a membrane filtration system can also be operatively connected parallel to a conduction element holding the process liquid so that a partial quantity of the process liquid out of the liquid stream of the process liquid can be used to form and filter the least one stream of the process liquid to be filtered per time unit. Here it can be advantageous if at least one adjustable splitting means or multiple co-operating splitting means are used to separate out a specifiable quantity of the process liquid from at least one element holding or conducting the process liquid in a controlled manner per time unit and to form at least one stream of the process liquid. In this way the partial quantity of process liquid separated out from a liquid stream of the process liquid per time unit can be specified and controlled in a precise manner. However, it is also advantageous here that the partial quantity of process liquid separated out per time unit can be adjusted to the current conditions and varied. In this way capacity bottlenecks can be avoided without having to accept significant compromises on quality or purity of the process liquid.

Regardless of the method of integration of a membrane filtration system into the device for treating food and containers, it can be useful to use or remove the partial quantities of process liquid for forming at least one stream of the process liquid to be filtered at a process liquid temperature of less than 80° C. and especially less than 50° C. This can considerably lengthen the operability/service life of the membrane filtration system. Above all, in this way the long-term stability of the actual filter elements of a membrane filtration system and especially the long-term stability of the actual filter membranes can be markedly improved. This is above all the case if the filter elements or filter membranes are made of plastic. This way a costly replacement of filter membranes or filter membrane modules can be avoided or delayed for as long as possible.

If other materials are used for the filter elements or filter membranes, e.g. if ceramic materials are used, the process liquid can also have higher temperatures such as 100° C. or more. Such temperatures are typical in, for example, superheated steam sterilization.

In a further development, however, it can also be provided that process liquid with a temperature between 40° C. and 50° C. be used to form at least one stream of the process liquid to be filtered. Particularly good filtration results can be achieved through membrane filtration or micro- and/or ultra-filtration at a process liquid temperature in this range. This is because, among other reasons, blockage of filter membranes due to lubricants such as paraffin or waxes can be avoided in this temperature range. Such lubricants are often used during manufacturing of containers, sometimes remain stuck to the containers after manufacturing, and can be introduced into the process liquid. Through membrane filtration of the process liquid in the stated temperature range, a process liquid with particularly low degree of contamination can be achieved.

Here it can also be provided that process liquid from a tempering-capable flow container be used to form at least one stream of the process liquid to be filtered. In this way the temperature of a stream of process liquid to be filtered can be purposefully set and the filtration efficiency maximized.

By recirculating a micro- or ultrafiltered stream of the process liquid at ambient pressure or in free fall back into at least one element holding or conducting the process liquid and/or into one treatment zone, the advantage is obtained that an additional conveying means for introducing or discharging a filtered stream into the process liquid is not needed. Micro- or ultrafiltration in a membrane filtration system necessarily leads to pressure loss across the filter system such that only low pressure exists in the outlet of the membrane filtration system. By conducting the filtered stream of the process liquid back in free fall, building additional pressure to force through a filtered stream can be omitted. This is also a variation that is structurally easy to realize.

It can be advisable here for a filtered stream of the process liquid to be at least partially fed into a liquid stream of the process liquid moved through a treatment zone after it acts on the food or containers. This variation of feeding a filtered stream into a treatment zone is advantageous in particular if a liquid stream of the process liquid is introduced into the treatment zone under a certain pre-existing pressure. The pre-existing pressure may be needed, for example to atomize the process liquid in order to spray the containers as evenly as possible in the treatment zone. This variation on introducing a filtered stream is also advisable, for example, to avoid unwanted influence of the filtered stream on the food and containers in the treatment zone. This may happen, for example, because of an unsuitable temperature level of the filtered stream of the process liquid.

However, it can also be advisable for filtered stream of the process liquid to be at least partially fed into a liquid stream of the process liquid moved through a treatment zone before it acts on the food or containers. This in particular allows a process liquid with very high quality or purity and very low bacterial count to be provided for treating the food and containers in a treatment zone.

In the method for treating food and containers, at least partial feeding of a filtered stream of the process liquid into a treatment zone arranged at the end of the process to receive the products can be particularly advantageous in order to rinse or clean the outside of the closed containers filled with food product. Such a process step is typically performed near the end of a method for treating food and containers, then a drying step or other secondary treatment step may potentially still follow. In such a process step for rinsing and washing containers, dirtying and/or contamination of the process liquid are particularly critical because under some circumstances dirt residues like bacteria or bacterial residues can remain on the surface of the container. This is why feeding a stream that has been filtered and cleaned by a membrane filtration system into such a treatment zone for rinsing containers is advantageous.

However, it can be just as practical if a filtered stream of the process liquid is at least partially fed into a treatment zone for cleaning and rinsing the inside and outside of unfilled containers placed at the inlet in the method for treating food and containers for holding food. Here, too, a process liquid with high purity can be used to treat the containers.

Another practical procedural step can be implemented if a stream of the process liquid is fed into a receiving container after filtration by the membrane filtration system and recirculated back into at least one element holding or conducting the process liquid and/or into a treatment zone via an outlet or equivalent element arranged on the receiving container. In this way a filtered reservoir of process liquid is collected or prepared that can be used for various purposes.

For example, a practical use for the process liquid filtrate collected in a receiving container can be achieved on one variation of an embodiment of the method by separating a membrane filtration system from the rest of the device for treating food and/or containers at specifiable time intervals during ongoing operation to clean the filter membranes and by feeding the process liquid filtrate collected in the receiving container through a membrane filtration system by reversing the flow direction through the filter membranes in comparison to filtration, i.e. the membrane filtration system is also cleaned by backflushing the filtrate. During continuous filtration of partial streams of the process liquid, residues naturally form on the filter membranes and modules over time. Particularly small particles can also penetrate into a filter membrane or a pore channel of a filter membrane and remain there. If micro-organisms have penetrated, growth of e.g. bacterial colonies can also lead to contamination of a filter membrane. Such a process is generally called "fouling" or "bio-fouling." Overall, residues on the membrane surface and/or particles or substances that have penetrated into and remained in a membrane lead to blockages on and in a membrane and therefore to shrinking flow capability and a reduction of the filtration performance of a filter membrane. The disclosed periodic cleaning of the filter membrane module by the collected process liquid filtrate achieved by reversing the flow direction can prevent blockages and closure of membrane pores as much as possible. Backflushing can be additionally assisted by inputting gas, for example by inputting compressed air into a filter membrane module. In addition, any potentially necessary sterilizations of a filter membrane, e.g. by chlorine, or even an expensive replacement of filter membranes or membrane modules can at least be postponed as long as possible. Finally, introducing antimicrobial silver nanoparticles into the filter membranes to prevent contamination of a filter membrane can be avoided or the use of silver nanoparticles can at least be considerably reduced.

Contaminated liquid waste is formed in the course of cleaning by reversing the flow direction through the filter membranes of the membrane filtration system. It can be useful to discharge this liquid waste directly from the device for treating food and containers and replace it with a corresponding quantity of fresh process liquid.

It can further be advantageous to admix chemicals from one or more chemical sources using a dispensing device into a stream of the process liquid to be filtered or a filtered stream or filtrate of the process liquid if needed both in treatment and in filtration and in cleaning for the membrane filtration system. If the dispensing device is suitably arranged, for example in a diverting element for a filtered stream of the process liquid or a bypass or backflush piping linked to the diverting element, admixing from the same chemical sources can take place both in treatment and in cleaning for the membrane filtration system. The type of chemicals to be used depends on the particular need and the feeding of chemicals can be performed by an operator of the device or an automatic control device for the device as needed. Since the addition of chemicals is possible in both filtration and cleaning, a flexible, targeted dispensation of chemicals from the same chemical sources can be performed as needed. Examples of chemicals that are suitable for both cases are surfactants for general cleaning or chlorine for disinfection of the filter membranes or other elements of the device for treating food and containers. Other typically used chemicals include, for example, organic acids for pH value stabilization, chelating agents, corrosion inhibitors, and biocides.

It can further be practical to feed a filtered stream through an adsorption device after the membrane filtration in filtration mode in order to remove or separate dissolved, suspended, or dispersed substances. In particular, in this way unwanted, uncoagulated parts can be removed from the process liquid that cannot be removed by the membrane filtration system.

For the highest possible process security, it can be advantageous to continuously monitor the quality or purity of the process liquid using suitable sensors, at least in the feed lines and/or drains of a treatment zone and/or in a treatment zone. In particular, measurements of turbidity can be useful to determine the purity of the process liquid and the particle concentration in the process liquid. Alternatively and/or additionally, measurements on random samples of the process liquid are also useful, especially to record fluctuations in the content of bacterial cultures and determine micro-organism growth rates.

Another advantage arises in a design variation in which a stream of the process liquid to be filtered is formed as needed out of different conduction elements containing or conducting process liquid, is filtered by at least one membrane filtration system, and after the membrane filtration process a filtered stream is fed into at least one conduction element holding or conducting process liquid and/or at least one treatment zone. It can particularly be advantageous to integrate a membrane filtration system into the device for treating products and/or containers using mechanical switching and/or splitting means in such a way that a membrane filtration system can be assigned different and/or multiple different conduction elements for holding or conducting the process liquid and/or treatment zones. The possibility of inlet-side switching of a membrane filtration system to different sources of process liquid for forming a stream to be filtered allows quick and efficient reactions to zone-specific fluctuations in the quality and degree of contamination of the process liquid in a flexible manner, especially to fluctuations in the particle concentration. This way there exists a fundamental option of switching from one process liquid source to another process liquid source, i.e. of using different liquid streams in different conduction elements to form the stream to be filtered. If desired, however, multiple liquid streams of the process liquid can also be used simultaneously to form a stream of the process liquid to be filtered. In this case, the stream to be filtered is formed by mixing the used/removed partial quantities from the different liquid streams of the process liquid.

Also practical is a variation of the embodiment in which the stream of the process liquid is formed for filtration by a membrane filtration system by switching between or mixing of different liquid streams of the process liquid from different conduction elements depending on measured values obtained by in-line measurements and/or random sample measurements. It can also be advantageous to recirculate a filtered stream of the process liquid into different conduction elements or treatment zones, depending on measured values obtained by in-line measurements and/or random sample measurements, by feeding or distributing the filtered stream of the process liquid into different liquid streams of the process liquid.

Finally, a design variation can be practical in which a treatment zone is assigned more than one membrane filtration system and a certain quantity is removed from the liquid streams of the process liquid fed into a particular treatment zone as needed to form a stream of the process liquid to be filtered and a filtered stream is filtered by one or more membrane filtration system(s) assigned to a treatment zone. By this measure, filtration can be continued even if one of the membrane filtration systems must be separated from the device for treating products and/or containers for purposes of potentially necessary repair and/or maintenance.

However, the aim of the invention is also achieved by providing a device for treating food and/or treating containers for holding food using a process liquid in which at least one membrane filtration system is included.

The device comprises at least one treatment zone for treating the food and/or the containers, a means of transport for transporting the food and/or containers through the treatment zone(s), and conduction elements for feeding liquid streams of the process liquid into a treatment zone and conduction elements for discharging liquid streams of the process liquid out of a treatment zone. The device further comprises additional conduction elements for holding and/or conducting the process liquid in the device and at least one conveying means for conveying liquid streams of the process liquid in the conduction elements, wherein the conduction elements are designed and arranged such that the process liquid for treating the foodstuffs can be at least partially recirculated back into the treatment zone or into the treatment zones.

In particular, the device includes at least one membrane filtration system that is arranged in the device and operatively connected to the conduction elements and/or to the treatment zones such that at least some or all of the total process liquid conducted through all existing treatment zones per time unit can be used to form at least one stream of the process liquid, the resulting stream or resulting streams are filtered by the at least one membrane filtration system and a filtered stream of the process liquid can be at least partially recirculated into one conduction element and/or one treatment zone.

Through these measures, a device can be prepared that is eminently suitable especially for the removal of impurities or contaminants with a very small particle size such as micro-organism colonies from the process liquid. This allows a significant improvement to be achieved compared to known devices, which are of only limited or even of no use in removing small particles from an at least partially recirculated process liquid. In addition, such a device can effectively impede contamination of the process liquid conducted through all existing treatment zones. Advantageously, the micro- or ultrafiltration via the at least one membrane filtration system can be performed during ongoing operation and is comparatively efficient and energy-saving.

The further characteristic that at least one treatment zone is designed for application of the process liquid on the outside of closed containers, wherein the process liquid flows around the outside of a closed container, is a particularly efficient construction characteristic for treating foodstuffs, since an already finished and filled trade product can be put out after the treatment. In addition, in this way the risk of recontamination of the foodstuffs in a filling zone placed after the treatment zone(s) can be precluded and/or a filling zone placed after the treatment zones is made superfluous.

The process liquid can be heated by arranging or designing at least one heating means in the device. As a result of this, the heated process liquid can be used to purposefully heat the food and containers. In addition, in this way the temperature of the process liquid can be set to a temperature level suitable for pasteurization of the food at least for one or more treatment zones before feeding the process liquid into the relevant treatment zone.

The process liquid can be cooled by arranging or designing at least one cooling means in the device. As a result of this, the cooled process liquid can be used to purposefully cool the food and containers.

In addition, it can be an advantage to arrange at least one treatment zone for heating the food and/or containers, at least one treatment zone for pasteurizing the food, and at least one treatment zone for cooling the foods and/or containers in succession. This design can provide a device for treating food and containers in which the food can be pasteurized particularly gently and damage to the pasteurized food can be effectively prevented.

It can further be advisable to design the device in such a way that the number and filtration capacity of the membrane filtration system(s) are fixed such that the total process liquid quantity drawn out of at least one element containing and/or conducting the process liquid per time unit for forming at least one stream of the process liquid to be filtered during continuous treatment can be chosen such that the filtration of the stream or the streams can achieve a removal rate of micro-organisms that is greater than the growth rate of these micro-organisms in the process liquid in the same time interval. This characteristic creates a device in which the membrane filtration system(s) can keep the total quantity of micro-organisms in the process liquid as low as possible and an increase in the total quantity of micro-organisms in the process liquid during continuous treatment of the food and/or containers is effectively prevented.

In addition, a design of the device can be useful in which the number and filtration capacity of the membrane filtration system(s) is fixed such that, based on the total quantity of process liquid conducted through all existing treatment zones per time unit, at least 1% and less than 25% per time unit can be used to form at least one stream and this partial quantity of the process liquid formed per time unit can be filtered by the membrane filtration system(s). This can ensure on the one hand that a sufficiently high number of impurities, especially small particles, are removed from the process liquid during ongoing treatment. On the other hand, this can also avoid overly laborious structural design of a membrane filtration system or the use of a large number of membrane filtration system(s). It is preferable to set the number and total filtration capacity of the membrane filtration systems such that—based on the total process liquid conducted through all existing treatment zones per time unit—between 2% and 10%, and especially between 2.5% and 7% per time unit is used to form at least one stream of the process liquid to be filtered and this partial quantity of the process liquid formed per time unit is filtered by at least one membrane filtration system.

It can additionally be useful to set the number and filtration capacity of the membrane filtration system(s) such that the total volume of process liquid in the device for treating food and/or containers can be filtered at least 1 time and preferably between 2 times and 10 times per day using the membrane filtration system(s). This design of the device for treating food and containers can ensure that depending on various process parameters, for example on the initial quality of the process liquid, the contamination rate existing in the treatment method itself, and especially the microorganism growth rate in the process liquid, a sufficient quantity of the process liquid can be cleaned by the membrane filtration system(s).

A membrane filtration system can in principle be connected on the inlet side both in series and in parallel with an element holding or conducting the process liquid. It can be an advantage here to arrange at least one adjustable splitting means and/or multiple co-operating splitting means on the inlet side of a membrane filtration system for controlled removal of a specifiable process liquid quantity per time unit out of at least one conduction element holding or conducting the process liquid and for formation of a stream of process liquid to be filtered. This design feature allows the partial quantity removed from a liquid stream of the process liquid per time unit to be controlled very precisely and adjusted to the particular immediate conditions.

It can further be advantageous for forming a stream of the process liquid to be filtered to operatively connect the at least one membrane filtration system to places with conduction elements where the process liquid held or conducted in the conduction elements has a temperature of less than 80° C. and especially less than 50° C. This way the operability and service life of a membrane filtration system can be considerably extended, especially if the filter elements or filter membranes are made of plastic. If other materials are used for the filter elements or filter membranes, e.g. if ceramic materials are used, the process liquid can also have higher temperatures such as 100° C. or more. Such temperatures are typical in, for example, superheated steam sterilization.

In a further development it can be provided that a feeding element of a membrane filtration system be connected to a tempering-capable flow container for the process liquid. This way the temperature of a stream of process liquid to be filtered can be purposefully set using the tempering-capable flow container and the filtration efficiency optimized.

Another design of the device that can be advantageous is one in which, to recirculate a filtered stream of the process liquid after completed filtration, draining elements out of at least one membrane filtration system are connected to at least one conduction element and/or at least one treatment zone in such a way that the at least one filtered stream of the process liquid can be fed into the conduction element(s) and/or the treatment zone(s) under the influence of gravity in free fall. This makes it possible for an additional conveying means for bringing in or away a filtered stream of the process liquid to be made superfluous, resulting in a structurally simple to realize variation and an efficient variation of the device.

For example, at least one membrane filtration system can be operatively connected on the inlet side to an opening in a treatment zone such that a filtered stream of the process liquid can flow off into the treatment zone. The opening in a treatment zone can be placed, for example, on an upper end of the treatment zone such that a filtered stream of the process liquid can be at least partially fed into a liquid stream of the process liquid that is moved through a treatment zone before it acts on the food and containers. On the other hand, however, it can also be practical to place the opening at a lower end of the treatment zone to avoid unwanted, e.g. thermal influence of the filtered stream on the food and containers in the treatment zone.

Another advantageous design of the device can be provided by designing at least one treatment zone for rinsing the outside of closed containers filled with foodstuffs, which at least one treatment zone is placed at the end of the treatment zone line in the transport direction of the containers through the treatment zones and which is connected to at least one draining element of a membrane filtration system in order to rinse the containers by feeding in a filtered stream of the process liquid. This provides a treatment zone for the final cleaning of the outside of the containers using a filtered stream of the process liquid in which the outside of the containers can be rinsed by a process liquid with very high purity and with low germ content.

It can, however, also be useful to arrange at least one treatment zone for cleaning the inside and outside of unfilled and open containers in the device for treating the food and containers, which at least one treatment zone is placed at the start of the treatment zone line in the transport direction of the containers through the treatment zones and which is connected to at least one draining element of a membrane filtration system in order to clean the containers by feeding in a filtered stream of the process liquid. This design variation of the device creates a treatment zone in which the containers can be treated with a process liquid with high purity.

A variation of the design in which a receiving container with an overflow is arranged in a draining element of the at least one membrane filtration system can also be of advantage. This way a filtered reservoir of process liquid can be collected and provided to be used for various purposes.

For the purposes of cleaning a membrane filtration system, it can for example be advisable to place closures in the feeding elements and draining elements to operatively separate the at least one membrane filtration system from the rest of the device and to place at least one conveying means in the receiving container and/or backflush piping extending between the receiving container and the draining element of the membrane filtration system that is designed to transport the process liquid filtrate collected in the receiving container in the opposite direction—compared to the flow direction through the filter membranes during filtration—through the at least one membrane filtration system. In this way, a membrane filtration system can be cleaned through backflushing using the filtrate during ongoing treatment by the device for treating the food and containers. This way e.g. blockages in a membrane or the closure of pores in a membrane can be prevented as much as possible without having to interrupt the treatment.

However, filtration can also be performed during backflushing/cleaning if multiple systems are operated at the same time/in parallel.

It can further be practical to discharge the liquid waste accrued in the course of cleaning by reversing the flow direction through the filter membranes of the membrane filtration system, to assign at least one closable liquid waste line to the membrane filtration system, and to place at least one closable feed device in the device to replace the discharged liquid waste with fresh process liquid. This makes it possible to discharge the liquid waste directly from the device for treating food and containers and replace it with a corresponding quantity of fresh process liquid.

It can also be useful to place a dispensing device in a draining element and/or in the backflush piping of the at least one membrane filtration system through which the process liquid or a filtrate of the process liquid can be admixed with chemicals from one or more chemical sources both during filtration and when cleaning the membrane filtration system. By installing a dispensing device connected to the chemical source(s), chemicals like chloride, biocides, surfactants, and other active chemicals can be admixed with the process liquid as needed both during filtration and when cleaning a membrane filtration system.

Additionally, a design can be advantageous in which an adsorption device is placed in a drainage element for draining a filtered stream of process liquid out of a membrane filtration system. In this way unwanted, uncoagulated parts can be removed from the process liquid that cannot be removed by the membrane filtration system. For example, carbon compounds can be removed from the process liquid using activated charcoal in such an adsorption device.

For better process security, it can be useful to place sensors in conduction elements and/or in treatment zones for continuous monitoring of the degree of contamination, especially by measuring the turbidity of the process liquid. This way the degree of contamination of the process liquid can be recorded and continuously monitored at least in sections.

Another advantageous design can be formed by assigning at least one switching means to a feeding element of a membrane filtration system that is operatively connected to at least two different conduction elements holding the process liquid in such a way that the stream of process liquid to be filtered can be formed as desired either from one of the liquid streams or multiple liquid streams of the process liquid in the conduction elements or from multiple liquid streams of the process liquid. This allows the membrane filtration system to be switched on the inlet side to different sources of the process liquid to form a filtered stream. In this way, for example, quick and efficient reactions are possible to zone-specific fluctuations in quality and degree of contamination of the process liquid, especially to fluctuations in the particle concentration.

Another design that is of advantage can be formed by assigning at least one mixing means to a feeding element of a membrane filtration system that is operatively connected to at least two different conduction elements holding the process liquid in such a way that a stream of process liquid to be filtered can be formed as desired either from one of the liquid streams or multiple liquid streams of the process liquid in the conduction elements or a stream of the process liquid to be filtered by the membrane filtration system can be formed by removing and mixing specifiable partial quantities from multiple liquid streams of the process liquid. This allows simultaneous removal of partial quantities of process liquid from different conduction elements and the formation of a stream of the process liquid to be filtered by mixing the removed partial quantities of process liquid.

However, it can also be advisable to assign at least one switching means to a draining element of a membrane filtration system that is operatively connected to at least one conduction element holding process liquid and/or at least one treatment zone in such a way that feeding a filtered stream of the process liquid into the at least one conduction element and/or the at least one treatment zone can be controlled. In this way a filtered stream of the process liquid can be fed as needed into one or more conduction element(s) and/or one or more treatment zone(s). This can be practical, for example, to set specific temperatures in sections for the process liquid in the device for treating food and containers. In general, this design can provide a device in which a filtered stream of the process liquid can be directed into different conduction elements or treatment zones as needed.

However, another design variation can be of advantage in which at least one splitting means is assigned to a draining element of a membrane filtration system which is operatively connected to at least one conduction element holding the process liquid and/or at least one treatment zone in such a way that feeding a filtered stream of the process liquid into the at least one conduction element and/or the at least one treatment zone can be controlled or specifiable quantities of the filtered stream of process liquid can be fed into the at least one conduction element and/or the at least one treatment zone. This characteristic can provide a device in which the purposeful feeding of specific partial quantities of a filtered stream of the process liquid into various conduction elements and/or treatment zones in a controlled manner is facilitated.

Finally, the aim of the invention is also achieved by using a membrane filtration system for continuous recycling of a process liquid in a device for treating food and containers for holding food using the process liquid. This way the process liquid in the device for treating food and containers for holding food can be continuously cleaned in a particularly efficient way.

BRIEF DESCRIPTION OF THE DRAWINGS

To facilitate better understanding of the invention, it will be explained in detail using the figures below.

Extremely simplified, schematic depictions show the following.

DETAILED DESCRIPTION OF THE PREFERRED EMBODIMENTS

In introduction, let it be noted that in the variously described embodiments, identical parts are provided with identical reference signs or identical part names, and that the disclosures contained in the description as a whole can be carried over analogously to identical parts with identical reference signs or identical part names. Likewise, positional information selected in the description, e.g. above, below, on the side, etc. refer to the directly described and depicted figure and if the position is changed, this positional information carries over analogously to the new position.

Figure 1:
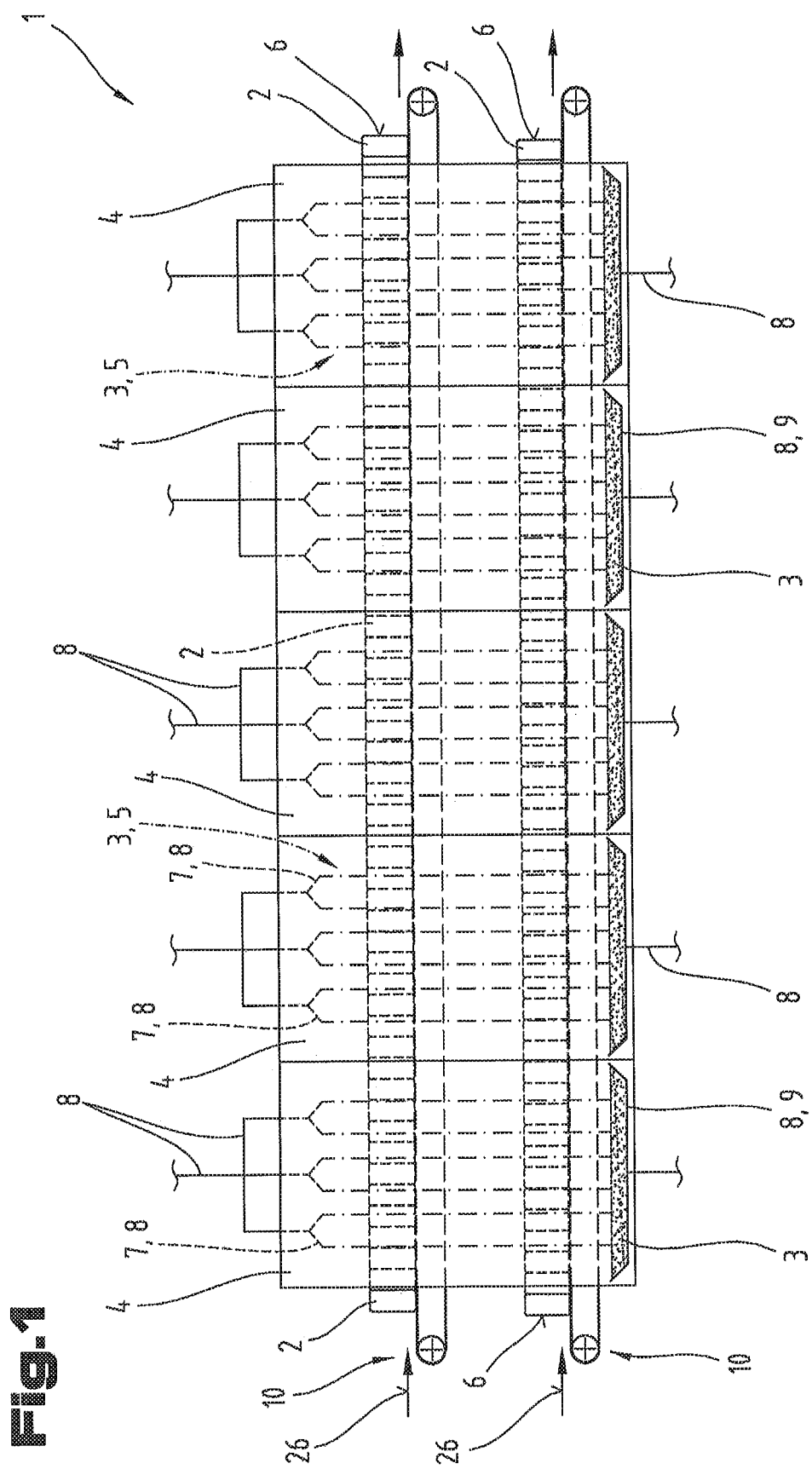
FIG. 1 An example embodiment of a known device for treating food and/or containers with treatment zones in an extremely simplified, schematic, and not-to-scale depiction.

FIG. 1 shows an example of an arrangement of treatment zones of a device 1 for treating food and/or treating containers 2 for holding food in a schematic and extremely simplified depiction. The food and containers 2 are treated by a process liquid 3 in at least one treatment zone 4. In the example embodiment shown in FIG. 1 the foodstuffs to be treated are located in closed containers 2 and are treated using a process liquid 3 by having a liquid stream 5 of the process liquid 3 flow around the outside 6 of the containers 2. In the example embodiment depicted in FIG. 1, the liquid stream 5 of the process liquid 3 through a treatment zone 4 is generated by the process liquid 3 being split by splitting devices such as spray nozzles 7 on the top of the treatment zone 4 and the liquid stream 5 of the process liquid 3 traversing the treatment zones 4 from top to bottom. A liquid stream 5 of the process liquid 3 is fed into a treatment zone 4 using structurally suitable conduction elements 8 like piping connected to the spray nozzles 7. In an analogous manner, after passing through a treatment zone 4 a liquid stream 5 of the process liquid 3 is removed from a treatment zone 4 again by means of other conduction elements 8 assigned to the bottom of a treatment zone 4. The conduction elements 8 provided to drain a liquid stream 5 of the process liquid 3 out of a treatment zone 4 can be formed by, for example, collecting tubs 9 that collect the liquid stream 5 of the process liquid 3 sprinkling through a treatment zone 4 at the bottom of the treatment zone 4. The process liquid 3 caught by the collecting tubs 8, 9 can then be discharged out of a treatment zone 4 by conduction elements 8 or piping 8 connected to the collecting tubs 8, 9, as shown schematically in FIG. 1.

The containers 2 can be transported through the treatment zones 4 using suitable means of transport 10 such as conveying means belts or the like, e.g. on two levels from left to right as shown in FIG. 1 by the arrows 26.

Alternately to the embodiment shown in FIG. 1, a treatment zone for treating the food using a process liquid can naturally be created in other ways as well. For example, a treatment zone for treating a liquid foodstuff can be designed as a heat exchanger in which the liquid foodstuff and the process liquid are conducted past each other while materially separated, as is for example typical when pasteurizing milk. The description of the invented device 1 using the embodiment shown in FIG. 1 is continued below, though it is noted at this juncture that the invention is not limited to the example embodiments specifically depicted below but also comprises alternative designs.

In the example embodiment shown in FIG. 1, the two treatment zones 4 depicted on the left side in FIG. 1 can be used e.g. for successive heating of the containers 2 or the food found in the containers. The treatment zone 4 depicted in the middle of FIG. 1 can be used e.g. for pasteurizing food and the two treatment zones 4 depicted on the right side in FIG. 1 can be used for sequential cooling of the food and containers. The corresponding treatment steps for heating, pasteurizing, and cooling can be executed by feeding a suitably tempered liquid stream 5 of the process liquid 3 in the relevant treatment zone 4. It can be practical for a liquid stream 5 to be fed into at least one treatment zone 4 for heating the food and/or containers at a temperature between 40° C. and 50° C.

Figure 2:
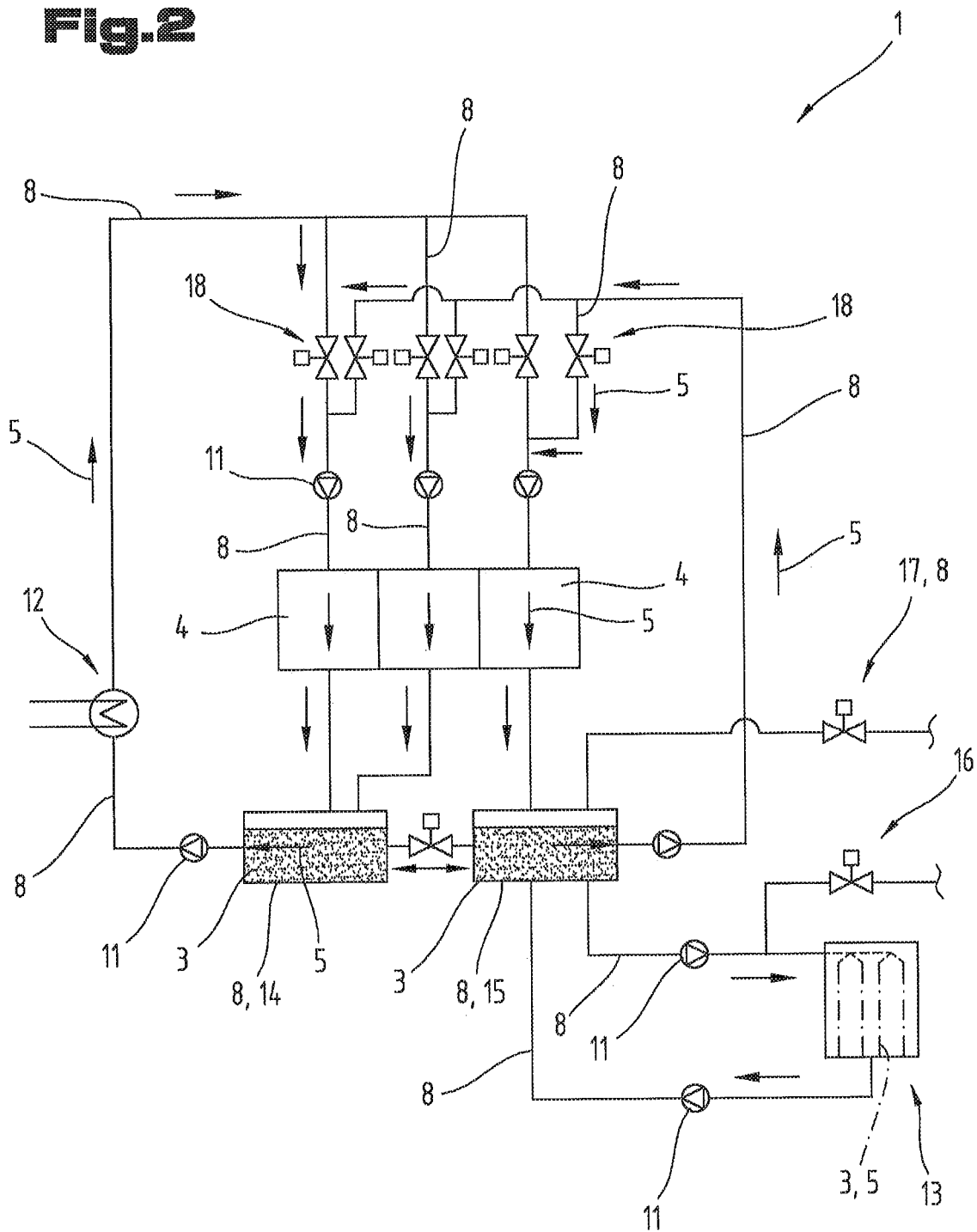
FIG. 2 A sample, well-known P&ID diagram of a device for treating food and/or containers in an extremely simplified depiction.

To feed a liquid stream 5 of the process liquid 3 into the relevant treatment zone 4, conveying means 11 can be assigned to the treatment zones 4 as can be seen in the flow diagram depicted in FIG. 2. To avoid unnecessary repetition, the same reference symbols and part names will be used for the same parts in FIG. 2 as in the preceding FIG. 1, with only three treatment zones 4 being depicted in FIG. 2 for greater clarity. The treatment zone 4 depicted in FIG. 2 left can again be used, for example, for heating the containers or food, while the treatment zone 4 drawn in FIG. 2 middle can be provided for pasteurization and the treatment zone 4 drawn in FIG. 2 right can be provided for cooling the containers and food.

The example embodiment of a flow diagram of a device 1 shown in FIG. 2 comprises a heating means 12 for heating the process liquid 3 and a cooling means 13 for cooling the process liquid 3. In the case of the example embodiment shown in FIG. 2, the process liquid 3 is fed into and/or conducted through the heating means 12 by an additional conveying means 11 out of a conduction element 8 in the form of a liquid tank 14 via conduction elements 8 in the form of piping or the like. The process liquid 3 in the heating means 12 can be heated in a great variety of ways, for example by heat transfer to the process liquid through a heating medium, for example saturated steam. In principle, any source of heat can be used to heat the process liquid 3, though it can be practical for pasteurizing food for the heating means 12 for heating the process liquid 3 to be set to a temperature of at least 80° C. After running through the heating means 12, the liquid stream 5 of the process liquid 3 heated in this way can be fed into the treatment zones 4 through conduction elements 8, e.g. piping.

Other methods for treating the food and containers are also conceivable alternately or additionally to the example embodiments shown in FIG. 1 and FIG. 2. For example, a process liquid, especially process water for treating food and/or containers can also be heated above the boiling point of the process water, so to a temperature above 100° C., and fed into a treatment zone as superheated steam. This may be practical for purposes of e.g. sterilization. In another example, dipping methods are also possible in which containers holding food are dipped into the process liquid.

To cool the process liquid 3, the process liquid 3 can be fed into the cooling means 13 as shown in FIG. 2, for example out of a liquid tank 15. In the example embodiment shown in FIG. 2, the cooling means 13 is connected to the liquid tank, for example a cold water tank 15, by conduction elements 8 in such a way that a liquid stream 5 of the process liquid 3 can be removed by a conveying means 11 from the liquid tank 15 and returned to the liquid tank 15 after completed cooling of the liquid stream 5 of the process liquid 3. The cooling means 13 can, for example, be executed as a cooling tower or heat exchanger in which the process liquid 3 is cooled by air or another cooling medium flowing in the opposite direction.

As can further be seen from FIG. 2, the conduction elements 8 for holding and conducting the process liquid 3 or the liquid streams 5 of the process liquid 3 in the device 1 are designed or arranged such that the process liquid 3 can be at least partially recirculated into the treatment zones 4 again. For better clarity, the flow directions for the liquid streams 5 of the process liquid 3 for the treatment mode of device 1 are indicated in FIG. 2 by arrows. Closable emptying devices 16 are provided to discharge a partial quantity of the process liquid 3 and at least one closable conduction element 8 designed as a feeding device 17 is arranged to feed in fresh process liquid 3. In the example embodiment shown in FIG. 2, flow regulator apparatuses 18 are provided in the conduction elements 8 placed on an inlet side of the treatment zones 4, by which flow regulator apparatuses 18 the liquid streams 5 of the process liquid 3 can be mixed at different temperature levels in a controlled manner. This makes it possible to purposefully set the temperature of the liquid streams 5 of the process liquid 3 separately for each treatment zone 4. In place of the depicted flow regulator apparatuses 18, three-way mixing valves or other suitable means can be provided for controlled mixing and setting of the temperature of a liquid stream 5 of the process liquid 3.

Of course, the example embodiment shown in FIG. 2 only shows one design of a device 1 for treating products and containers. For example, for some embodiments of devices for treating food and/or containers it is typical to feed a liquid stream directly into another treatment zone after it is drained from one treatment zone. This is useful, for example, if a liquid stream of the process liquid drained out of a treatment zone has a temperature level suitable for treating the food and/or containers in another treatment zone.

Figure 3:
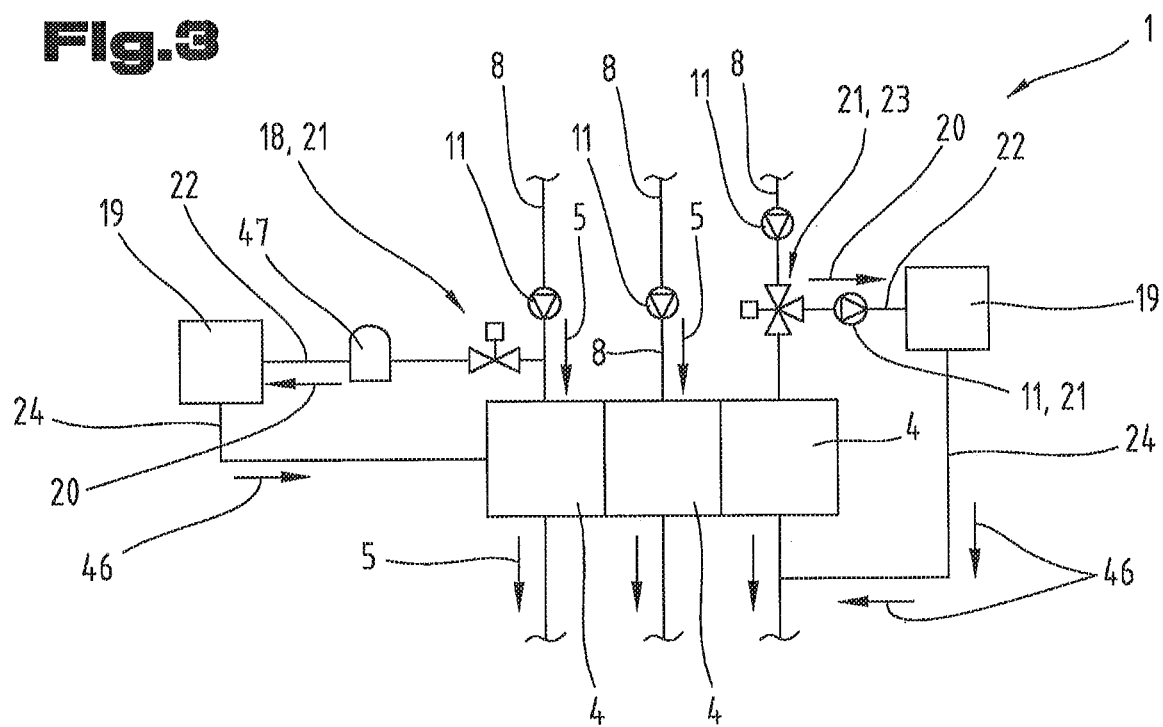
FIG. 3 Excerpts of a partial diagram of a device with membrane filtration systems in an extremely simplified depiction.

As shown in FIG. 3, the device 1 includes at least one membrane filtration system 19, wherein the at least one membrane filtration system 19 is arranged in the device 1 and operatively connected to the conduction elements 8 and/or to the treatment zones 4 such that at least some or all of the total process liquid conducted through all existing treatment zones 4 per time unit can be used and/or removed to form at least one stream 20 of the process liquid, the resulting stream 20 or resulting streams 20 are filtered by the at least one membrane filtration system 19 and a filtered stream 46 of the process liquid can be at least partially recirculated into one conduction element 8 and/or one treatment zone 4. FIG. 3 uses the same reference signs and part names for the same parts as were used in the preceding FIG. 1 and FIG. 2. To avoid unnecessary repetition, please refer to the detailed description in the above FIG. 1 and FIG. 2.

In principle, any given liquid stream 5 of the process liquid can be used to form a stream 20 of the process liquid to be filtered and/or partial quantities of the process liquid can be taken from any liquid stream 5 to form a stream 20 to be filtered. Likewise, a filtered stream 46 of the process liquid can in principle be returned to any conduction element 8 for the process liquid and/or to any treatment zone 4. However, certain variations of incorporating one or more membrane filtration system(s) 19 offer advantages that are explained in more detail below using additional example embodiments depicted in the figures.

It is preferable for the number and filtration capacity of the membrane filtration system(s) 19 in the device 1 to be fixed or designed such that the total process liquid quantity drawn out of at least one element 8 holding and/or conducting the process liquid per time unit for forming at least one stream 20 of the process liquid 3 during continuous treatment can be chosen such that the filtration of the stream 20 or the streams 20 can achieve a removal rate of micro-organisms that is greater than the growth rate of these micro-organisms in the process liquid 3 in the same interval.

The number and the filtration capacity of the membrane filtration system(s) 19 can also be chosen or fixed such that, based on the total quantity of process liquid conducted through all existing treatment zones 4 per time unit, at least 1% and less than 25% per time unit can be used to form at least one stream 20 to be filtered and this partial quantity of the process liquid formed per time unit can be filtered by the membrane filtration system(s) 19. A particularly advantageous design is one where, based on the total process liquid conducted through all existing treatment zones per time unit, between 2% and 10%, and especially between 2.5% and 7% per time unit is used to form at least one stream 20 of the process liquid and this partial quantity of the process liquid formed per time unit is filtered by at least one membrane filtration system 19.

Additionally, it is preferable to set the number and filtration capacity of the membrane filtration system(s) 19 such that the total volume of process liquid in the device 1 for treating food and/or containers can be filtered at least 1 time and preferably between 2 times and 10 times per day using the membrane filtration system(s) 19.

One option for forming and filtering a stream 20 of the process liquid is shown in FIG. 3, in which FIG. 3 e.g. two membrane filtration systems 19 are placed in a device 1 for treating food and/or containers of which excerpts are shown. FIG. 3 uses the same reference symbols and part names for the same parts as were used in the preceding FIGS. 1 and 2. To avoid unnecessary repetition, please refer to the detailed description in the above FIG. 1, 2.

In the example embodiment shown in FIG. 3, the two membrane filtration systems 19 depicted are placed bypass-like between a conduction element 8 conducting a liquid stream 5 and a treatment zone 4 (left in FIG. 3) or another conduction element 8 (right in FIG. 3). In the example embodiment shown, suitable splitting means 21 are used to remove a partial quantity of a liquid stream 5 of the process liquid per time unit to form a stream 20 to be filtered and to filter it using a membrane filtration system 19. In doing so, feeding element 22 of the membrane filtration system 19 can be operatively connected to a conduction element 8 for the process liquid or also to a treatment zone.

For controlled removal of a partial quantity out of the liquid stream 5 to form a stream 20, something like a splitting means 21 in the form of a flow regulator apparatus 18 can be placed in a feeding element 22 into a membrane filtration system 19, as shown on the left in FIG. 3. Alternately, as shown for example on the right in FIG. 3, a three-way splitting valve 23 can also be used as a splitting means 21. A splitting means 21 in the form of a conveying means 11 or pump can also be arranged to work together with a valve 18, 23 in order to allow controlled removal of a partial quantity of the process liquid out of the conduction element 8. In principle, a splitting means 21 designed as a conveying means 11 can also be used by itself. Preferably, however, the placement of an additional conveying means 11 in a feeding element 22 of a membrane filtration system 19 is omitted and, as shown on the left in FIG. 3, the removal of a partial quantity of the process liquid is accomplished using a conveying means 11 placed in a conduction element 8 of the device 1.

After completed filtration, a filtered stream 46 of the process liquid is recirculated into a treatment zone 4 like in the example shown on the left in FIG. 3 and/or into a conduction element 8 as in the example shown on the right in FIG. 3. A draining element 24 of a membrane filtration system 19 can again be operatively connected to a treatment zone 4 or to a conduction element 8 for the process liquid.

The treatment zone 4 shown on the left in FIG. 3 can again, for example, be designed as a heating zone for the food or containers, the treatment zone 4 shown in the middle of FIG. 3 can be for pasteurizing the food, and the treatment zone 4 shown on the right in FIG. 3 can be for cooling the food or containers. Accordingly, during ongoing treatment mode of the device 1 the pasteurization zone 4 placed in the middle is fed a liquid stream 5 of a high-temperature process liquid, while the treatment zones 4 for heating and cooling the food and containers are fed liquid streams 5 at comparably low temperatures.

As indicated in FIG. 3, in order especially to spare the membrane filtration system 19 a liquid stream 5 at a relatively low temperature can preferably be used to form a stream 20 of the process liquid to be filtered. In the example embodiment shown in FIG. 3, the feeding elements 22 of the depicted membrane filtration systems 19 are operatively connected to the conduction elements 8 leading to the heating and cooling treatment zones, i.e. the treatment zones 4 depicted on the left and right, respectively, in FIG. 3. The two conduction elements 8 to which the feeding elements 22 are connected each contain one liquid stream 5 with a relatively low temperature process liquid. It is preferable for forming a stream 20 of the process liquid to be filtered for the at least one membrane filtration system 19 to be operatively connected to conduction elements 8 at places where the process liquid held or conducted in the conduction elements 8 has a temperature of less than 80° C. and especially less than 50° C. It is preferable for the at least one membrane filtration system for forming a stream 20 of the process liquid to be filtered to be operatively connected to locations with conduction elements 8 of the device 1 in such a way as to ensure that process liquids with a temperature between 40° C. and 50° C. are used to form at least one stream 20 to be filtered. As has been shown, membrane filtration and the filtration performance of a stream 20 of process liquid is particularly efficient in this temperature range.

As is further shown in FIG. 3, it can further be provided that a feeding element 22 of a membrane filtration system 19 be connected to a tempering-capable flow container 47 for the process liquid. Such a flow container 47 can, for example, be designed as a buffer with integrated heat exchanger or as a buffer with integrated electric heating or the like. In this way a stream 20 to be filtered can be formed by using the process liquid from the flow container 47.

Figure 4:
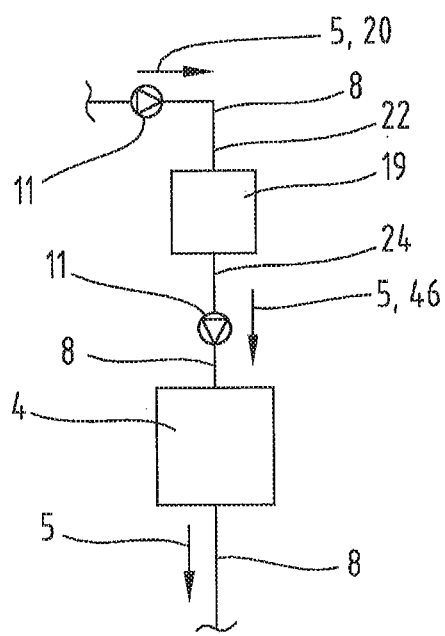
FIG. 4 Excerpts of another partial diagram of a device with membrane filtration systems in an extremely simplified depiction.

Alternatively to the example embodiment shown in FIG. 3, an entire liquid stream 5 of the process liquid can be used to form a stream 20 of the process liquid to be filtered, as is shown schematically in FIG. 4. In the example shown in FIG. 4, the membrane filtration system 19 is placed in series in a conduction element 8 leading to a treatment zone and/or its feeding element 22 and draining element are each connected to a conduction element 8 leading to a treatment zone 4. This way the entire liquid stream 5 of the process liquid 3 conducted through the conduction element 8 is directed through the membrane filtration system 19 and in the example shown in FIG. 4 fed into a treatment zone 4 after completed membrane filtration. In such an arrangement of a membrane filtration system 19, providing an additional conveying means 11 to bring the process liquid 3 into a treatment zone 4 after completed micro- and ultrafiltration can be necessary because of the loss of pressure over the membrane filtration system 19.

Figure 5:
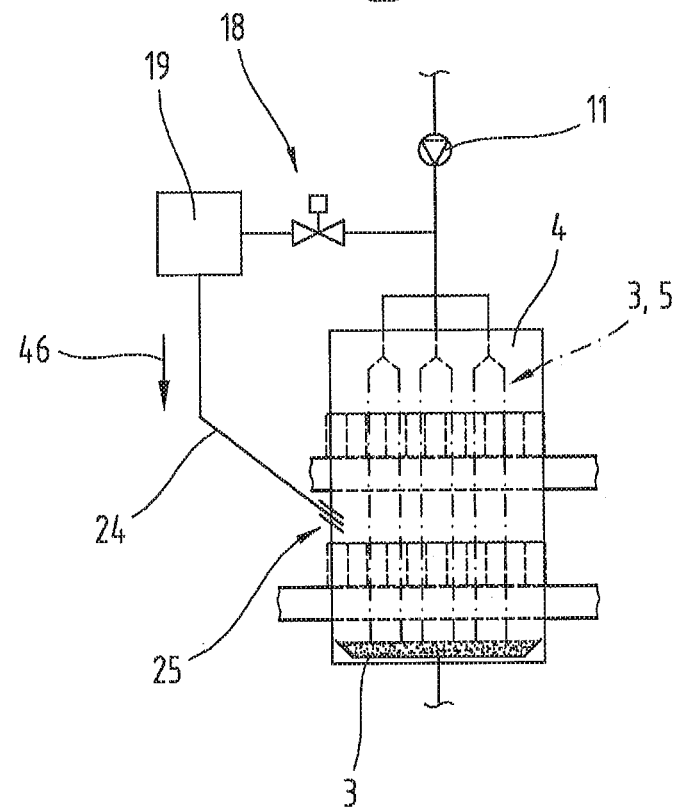
FIG. 5 Excerpts of another partial diagram of a device with membrane filtration systems in an extremely simplified depiction.

Advantageously, feeding a filtered stream 46 of the process liquid into a treatment zone 4 after completed filtration can be accomplished without a conveying means 11. For this purpose, it can be useful for the draining elements 24 of a membrane filtration system 19 to be connected e.g. to a treatment zone 4 in such a way that at least one filtered stream 46 of the process liquid can be fed into the treatment zone 4 under the influence of gravity, in free fall. Such an example embodiment is shown in FIG. 5; to avoid unnecessary repetitions, FIG. 5 once again uses the same reference signs and part names for the same parts as are used in the preceding FIGS. 1 and 4. FIG. 5 depicts an example embodiment of a technical connection of a membrane filtration system 19 to a treatment zone 4 in which a draining element 24 leading from the membrane filtration system 19 to the treatment zone 4 is arranged in such a way that a constant gradient from top to bottom in the direction from the membrane filtration system 19 to the treatment zone 4 is formed, as a result of which the stream 46 of the process liquid 3 conducted away from the membrane filtration system 19 to the treatment zone 4 and filtered can flow under the influence of gravity. To introduce the filtered stream 46 of the process liquid 3 into the treatment zone 4, one or more opening(s) 25 in the treatment zone 4 can or could easily be designed in the treatment zone 4 or connected to the draining elements 24 so that the filtered stream 46 can flow into the treatment zone 4.

Figure 6:
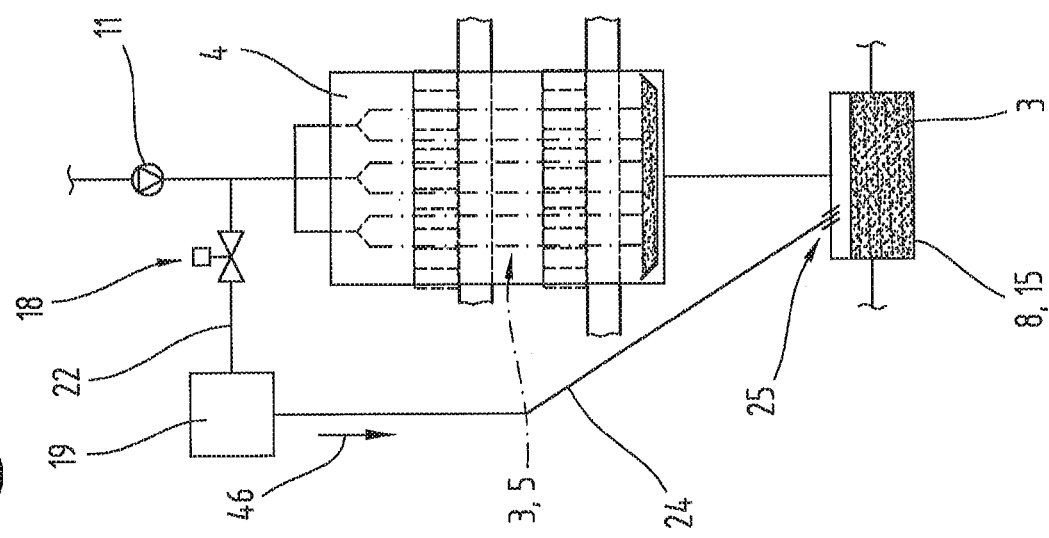
FIG. 6 Excerpts of another partial diagram of a device with membrane filtration systems in an extremely simplified depiction.

FIG. 6 depicts excerpts of another, potentially independent embodiment of the device 1, where once again the same reference signs and part names are used for the same parts as have been used in the preceding FIGS. 1 to 5. To avoid unnecessary repetition, please refer to the detailed description in the above FIGS. 1 to 5. FIG. 6 shows, in the example embodiment depicted in FIG. 5, an arrangement for feeding a filtered stream 46 of the process liquid 3 into a conduction element 8 for the process liquid 3, for example a liquid tank 15. The draining elements 24 again extend from top to bottom in a constant gradient from the membrane filtration system 19 down to the liquid tank 8, 15 so that the filtered stream 46 can flow through the opening(s) 25 in the liquid tank 8, 15.

Figure 7:
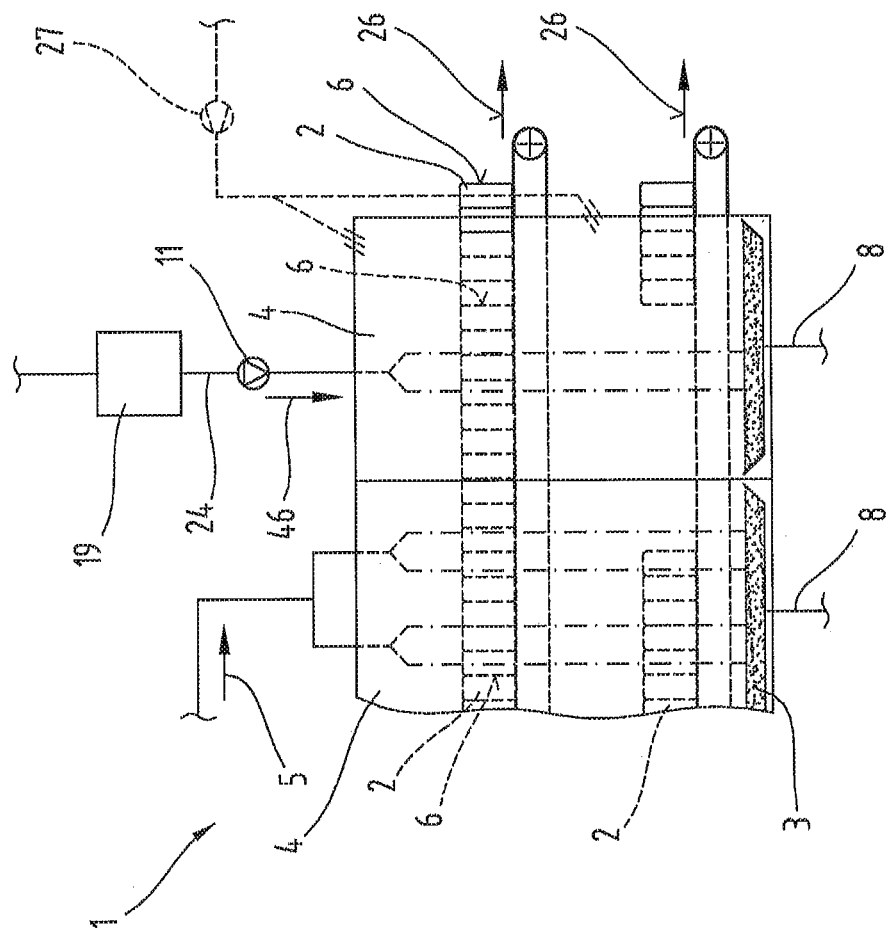
FIG. 7 Excerpts of another partial diagram of a device with membrane filtration systems in an extremely simplified depiction.

FIG. 7 depicts excerpts of another, potentially independent embodiment of the device 1, where once again the same reference signs and part names are used for the same parts as have been used in the preceding FIGS. 1 to 6. To avoid unnecessary repetition, please refer to the detailed description in the above FIGS. 1 to 6. In FIG. 7, a treatment zone 4 is arranged for rinsing the outside 6 of the closed containers 2 filled with food, which at least one treatment zone 4 is arranged at the end of the treatment zone line in the transport direction 26 of the containers 2 through the treatment zones 4. A filtered stream 46 of the process liquid 3 is fed into the treatment zone 4 to clean the containers 2. The treatment zone 4 is again operatively connected to a draining element 24 of a membrane filtration system 19 for this purpose. In addition, the treatment zone 4 can be assigned e.g. a fan 27 for drying the containers 2 with drying air or another drying device.

Figure 8:
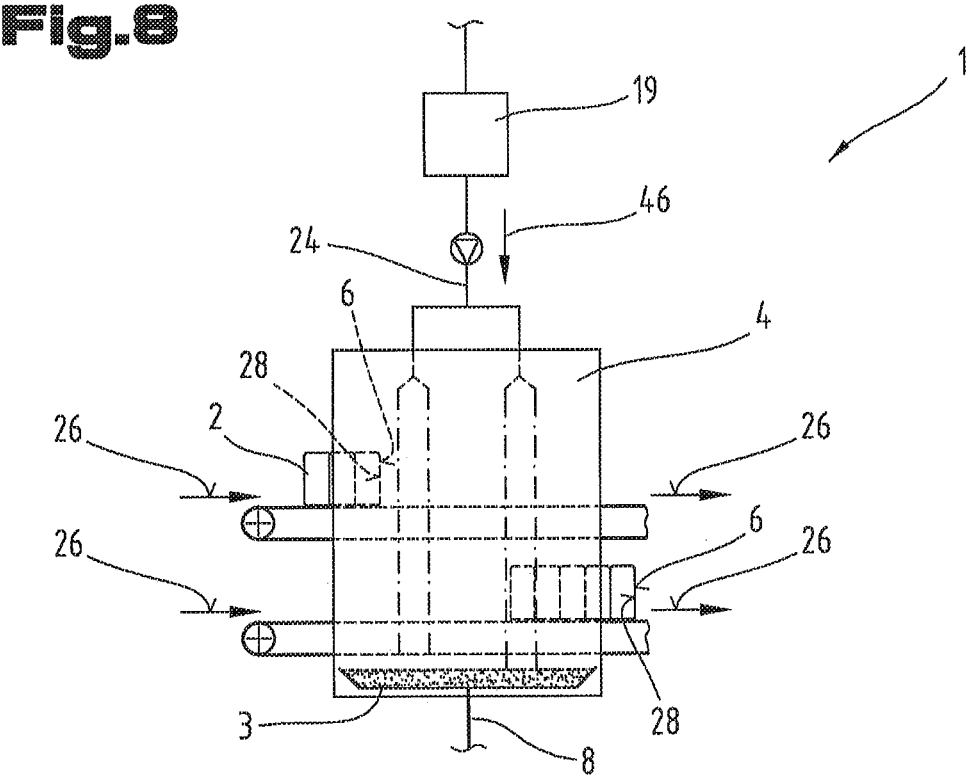
FIG. 8 Excerpts of another partial diagram of a device with membrane filtration systems in an extremely simplified depiction.

FIG. 8 depicts excerpts of another, potentially independent embodiment of the device 1, where once again the same reference signs and part names are used for the same parts as have been used in the preceding FIGS. 1 to 7. To avoid unnecessary repetition, please refer to the detailed description in the above FIGS. 1 to 7. FIG. 8 depicts a treatment zone 4 for rinsing or cleaning the inside 28 and the outside 6 of unfilled and open containers 2, wherein the depicted treatment zone 4 is arranged at the start of the treatment zone line in the transport direction 26 of the containers 2 through the treatment zones 4. A filtered stream 46 of the process liquid 3 is again fed into the treatment zone 4 to clean the open containers 2. The treatment zone 4 is again operatively connected to a draining element 24 of a membrane filtration system 19 for this purpose.

Figure 9:
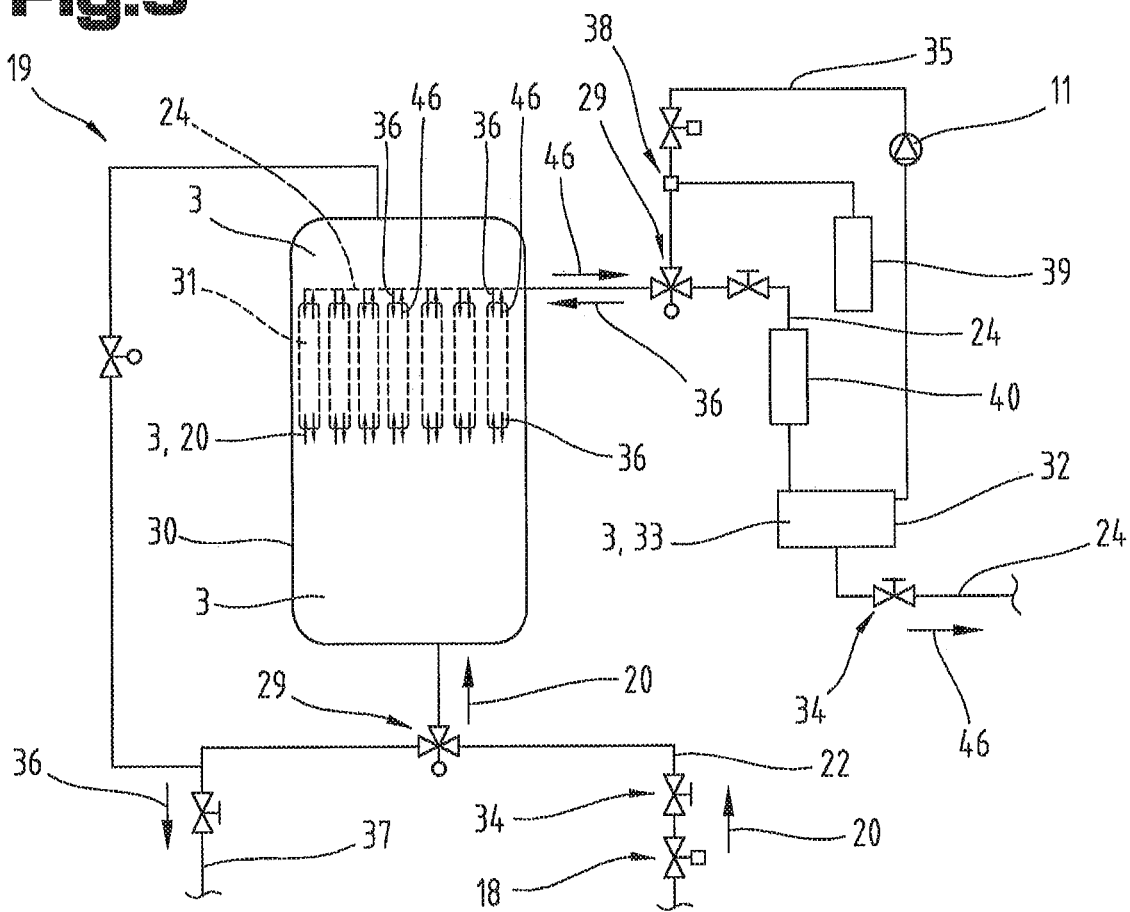
FIG. 9 An design of a membrane filtration system, schematic and in an extremely simplified depiction.

FIG. 9 depicts an example embodiment of a design of a membrane filtration system 19. To avoid unnecessary repetitions, please refer again to the detailed description in the preceding FIGS. 1 to 8, where the same reference signs and part names are used for the same parts as in the preceding FIGS. 1 to 8. As already explained in detail, during filtration the membrane filtration system 19 is fed a stream 20 of the process liquid 3 to be filtered through the feeding elements 22, wherein a partial quantity fed in per time unit can be specified e.g. using a flow regulator apparatus 18. The stream 20 of the process liquid 3 to be filtered can, for example, be directed by a three-way valve 29 into a pressure vessel 30 in which filter membrane modules 31 are arranged to filter the process liquid 3.

The filter membrane modules 31 shown in FIG. 9 can consist of a great variety of membranes. The construction of the membranes can be homogeneous or inhomogeneous and can exhibit different symmetries in cross-section. In particular, porous membranes in capillary or hollow fibre form and/or flat membranes can be used. The membranes can be made out of various materials. Examples of suitable membrane materials are polyethylene, polypropylene, polyether sulfone, polyvinylidene fluoride, ethylene propylene diene monomer (EDPM), polyurethane, or cellulose acetate. It is preferable to use membrane materials that are hydrophilic. Alternately and/or additionally to plastic membranes, ceramic materials can also be used to form the membranes of the filter membrane modules 31. Particularly suitable are chlorine-resistant membrane materials that can withstand a chlorine exposure of more than 200,000 ppm*h and preferably more than 2,000,000 ppm*h.

The depicted example embodiments show operation of the device 1 and the membrane filtration system (s) 19 under high pressure. Alternately or additionally, low pressure zones can also be arranged in at least sections of the device 1; running a membrane filtration system 19 at low pressure is particularly conceivable. For example, suction devices (not shown) can be placed in the draining elements 24, by which a filtered stream 46 of the process liquid 3 can be suctioned from a filter membrane module 31. For this reason, the filter membranes of the filter membrane modules 31 are preferably designed to withstand high and low pressure and suited for trans-membrane pressures and pressure differences of at least 1,000 mbar without permanent blocking of the membranes during ongoing operation of the membrane filtration system 19. Where needed, membranes suitable for pressures of e.g. 2,000 mbar and up to 5,000 mbar over the particular membrane can also be used. During filtration, the trans-membrane pressure difference should preferably be less than 5 bar, especially less than 2 bar, and particularly preferably 1 bar or less. It is preferable to use porous membranes, with the effective pore diameter of a particular membrane lying in a range between 0.01 µm and 1 µm, membranes with effective pore diameters between 0.05 µm and 0.5 µm are particularly suitable for the filter membrane modules 31 of the membrane filtration system (s) 19.

The example embodiment shown in FIG. 9 depicts what is called the "outside-in" mode of the membrane filtration system 19, in which the stream 20 of the process liquid 3 to be filtered enters the filter membrane modules 31 from outside during filtration, filters through the filter membranes of the filter membrane modules 31, and a filtered stream 46 of the process liquid 3 is drained out of the inside of the filter membrane modules 31 using draining elements 24. Alternately to the example embodiment shown in FIG. 9, there is also what is called "inside-out" operation in which a stream 20 of the process liquid 3 to be filtered is fed into the inside of the filter membrane modules 31 during filtration and a filtered stream 46 of the process liquid 3 exits on the outside of the filter membrane modules 31. In addition, both a so-called "cross-flow" mode and a cyclical "dead-end" interconnection are possible when it comes to the flow of the stream 20 of the process liquid 3 into a filter membrane module 31. Finally, submerged membrane configurations in which a filtered stream 46 of the process liquid 3 is suctioned off by low pressure are also possible. When a membrane filtration system 19 is in a submerged configuration, a cyclical or acyclical air bubble rinse or air turbulence can be provided or executed to counter the formation of a layer on the membrane surfaces.

In the example embodiment shown in FIG. 9, after the process liquid 3 passes through the filter membrane modules 31 and filtration is completed, the filtered stream 46 of the process liquid 3 is drained out of the membrane filtration system 19 through the draining elements 24 again. As shown in FIG. 9, it can be advisable here to place a receiving container with an overflow 32 in the drain 24, which depending on its dimensions is designed for temporary storage of a certain volume of the filtered process liquid 3 or a filtrate 33. In particular, this filtrate 33 of the process liquid 3 can be used to clean via flushing by reversing the flow direction through the filter membrane modules 31.

To run a cleaning mode for the filter membrane modules 31, closures 34 are placed in the feeding elements 22 and the draining elements 24 that permit mechanical separation of the membrane filtration system 19 from the other structural elements of the device for treating food and containers. In addition, at least one conveying means 11 is placed in the receiving container 32 and/or a backflush line 35 extending between the receiving container 32 and the draining elements 24 of the membrane filtration system 19. This way appropriate switching of the three-way valves 29 can reverse the flow direction in the membrane filtration system 19 such that the process liquid 3 flows through the filter membrane modules 31 in the reverse direction 36 than in filtration mode. To drain the liquid waste accrued in the course of cleaning by reversing the flow direction through the filter membranes of the membrane filter system 19, the member filter system 19 is assigned at least one closable liquid waste line 37. A quantity of fresh process liquid 3 equal to the drained quantity of liquid waste can, for example, be provided by the feeding device 17 for fresh process liquid 3 shown in FIG. 2.

As further shown in FIG. 9, a dispensing device 38 can be placed in a draining element 24 and/or in the backflush piping 35 of the one membrane filtration system 19 through which the process liquid 3 or the filtrate 33 of the process liquid 3 can be admixed with chemicals from one or more chemical sources 39 both during filtration and when cleaning the membrane filtration system 19. Chemicals can be admixed during filtration through the three-way valve 29 arranged in the drain 24. In addition, an adsorption device 40 can be placed in the drain 24 of the membrane filtration system 19 that allows removal or separation of substances dissolved, suspended, or dispersed in a filtered stream 46 of the process liquid 3.

Figure 10:
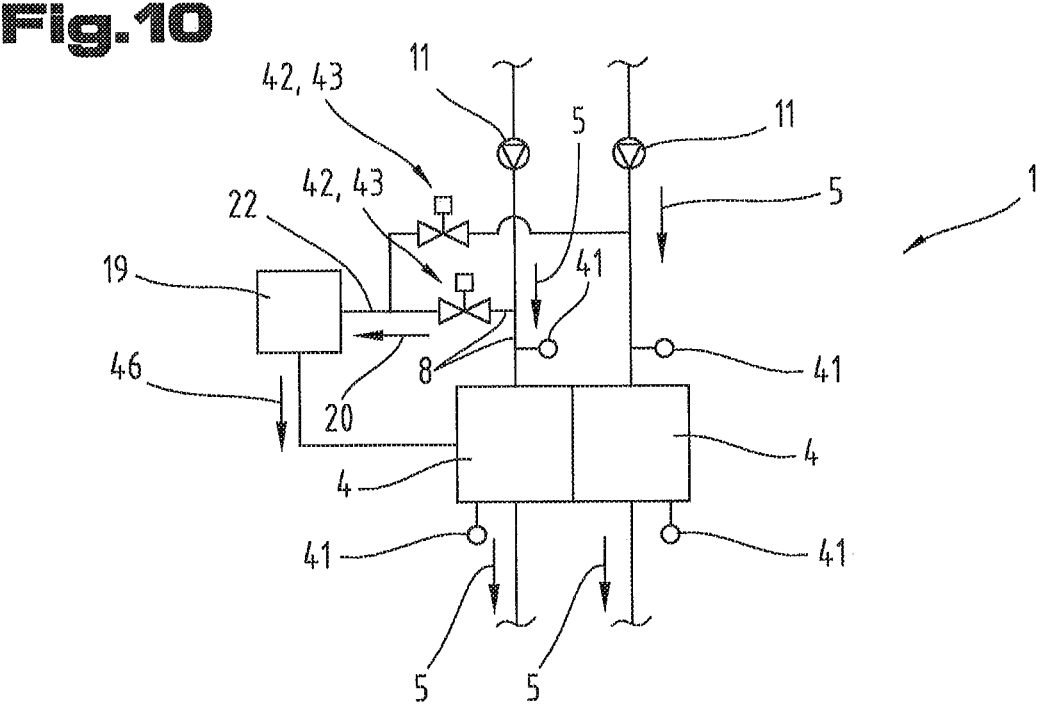
FIG. 10 Excerpts of another partial diagram of a device with membrane filtration systems in an extremely simplified depiction.

FIG. 10 depicts excerpts of another, potentially independent embodiment of the device 1, where once again the same reference signs and part names are used for the same parts as have been used in the preceding FIGS. 1 to 9. To avoid unnecessary repetition, please refer to the detailed description in the above FIGS. 1 to 9. FIG. 10 depicts sensors 41 that are designed for continuous monitoring of the degree of contamination, especially by measuring the turbidity of the process liquid. The sensors 41 can be placed in the conduction elements 8 and/or in the treatment zones 4 of the device 1.

The measured values of the sensors 41 can, for example, be used to assign a membrane filtration system 19 to different treatment zones 4 or conduction elements 8 for liquid streams of the process liquid via switching means and directing elements. Switching between conduction elements 8 and/or treatment zones 4 can naturally also be done based on measurements using random samples taken from the device 1.

For example, it can be provided that a stream 20 of the process liquid 3 is formed for filtration by a membrane filtration system 19 by switching between or mixing of different liquid streams 5 of the process liquid 3 from different conduction elements 8 depending on measured values obtained by in-line measurements and/or random sample measurements. It can further be provided that a filtered stream 46 of the process liquid 3 be recirculated into different conduction elements 8 and/or treatment zones 4 by introducing and/or splitting the filtered stream 46 into different liquid streams 5 depending on measured values obtained by in-line measurements and/or random sample measurements.

To switch a membrane filtration system 19 to different conduction elements 8, the feeding elements 22 of a membrane filtration system 19 can, for example, be assigned two switching means 42, 42, as shown in FIG. 10. The two depicted switching means 42, 42 are operatively connected to two different conduction elements 8, 8 holding the process liquid in such a way that a stream 20 of the process liquid can be formed for filtration either out of one of the two liquid streams 5, 5 of the process liquid in the conduction elements 8, 8 or out of both liquid streams 5, 5. For this purpose the two switching means 42, 42 can be designed as so-called "open-shut valves" so that each of the two switching means 42, 42 can operatively open or close the supply of process liquid into the membrane filtration system 19.

A suitable alternative to the example embodiment shown in FIG. 10 would naturally also be a single switching means 42 designed as a 3-way switching means (not shown in FIG. 10) for switching the feeding elements 22 of the membrane filtration system 19 to one of the two conduction elements 8. The switching means 42 designed as 3-way switching means 42 would again be assigned the feeding elements 22 of the membrane filtration system 19 on the one hand and connected to two different conduction elements 8, 8 on the other hand.

In FIG. 10 and below, the depiction and description using 2-way valves is maintained for better understanding, with it being noted at this juncture that the design and placement of a switchable membrane filtration system 19 can be arranged in numerous ways and is not limited to the example embodiments portrayed in FIG. 10 and below.

Instead of switching means 42, a feeding element 22 of a membrane filtration system 19 can also be assigned two mixing means 43, 43 as indicated in FIG. 10. The mixing means 43, 43 are again operatively connected to two different conduction elements 8, 8 holding the process liquid in such a way that the stream 20 of the process liquid can be formed for filtration again either out of one of the two liquid streams 5, 5 of the process liquid or out of both liquid streams 5, 5 in the conduction elements 8, 8 or by removing and mixing specifiable partial quantities from the two liquid streams 5, 5 of the process liquid. For this purpose, the mixing means 43, 43 can for example be designed as flow regulator valves.

Of course, a membrane filtration system 19 can also be assigned more than two switching means 42 and/or mixing means 43, which can accordingly be connected to more than two conduction elements 8.

Figure 11:
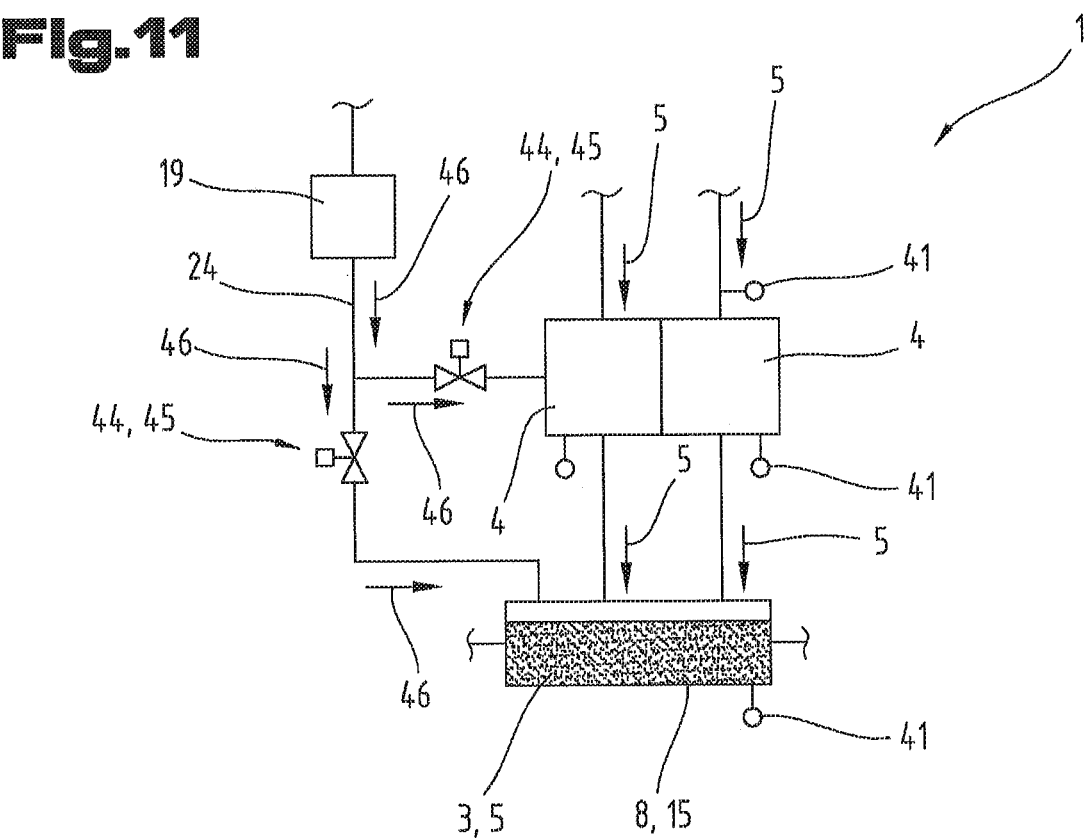
FIG. 11 Excerpts of another partial diagram of a device with membrane filtration systems in an extremely simplified depiction.

FIG. 11 depicts excerpts of another, potentially independent embodiment of the device 1, where once again the same reference signs and part names are used for the same parts as have been used in the preceding FIGS. 1 to 10. To avoid unnecessary repetition, please refer to the detailed description in the above FIGS. 1 to 10. In the example embodiment depicted in FIG. 11, a drain 24 of a membrane filtration system 19 is assigned two switching means 44, 44. A switching means is operatively connected to a conduction element 8 in the form of a liquid tank 15. The other switching means 44 is operatively connected to a treatment zone 4. This design can feed a filtered stream 46 of the process liquid 3 either into the conduction element 8 in the form of a liquid tank 15 or the treatment zone 4 or into both the conduction element 8 and the treatment zone 4.

For this purpose, the two switching means 44, 44 in FIG. 11 can again be designed as so-called "open/shut valves" so that each of the two switching means 44, 44 can operatively open or close the discharge of a filtered stream 46 out of the membrane filtration system 19 into the treatment zone 4 and/or the at least one conduction element 8.

Instead of switching means 44, a draining element 24 of a membrane filtration system 19 can also be assigned two splitting means 45, 45 as indicated in FIG. 11. A splitting means 45 is again operatively connected to a conduction element 8 in the form of a liquid tank 15. The other splitting means 45 is operatively connected to a treatment zone 4. Because of this design, the filtered stream 46 of the process liquid 3 can again be fed either into the conduction element 8 designed as a liquid tank 15 or the treatment zone 4. Alternately, the liquid tank 15 and the treatment zone 4 can each be fed specifiable partial quantities of the filtered stream 46 of the process liquid 3. For this purpose, the splitting means 45, 45 can for example again be designed as flow regulator valves.

Again, a membrane filtration system 19 can also be assigned more than two switching means 44 and/or splitting means 45, which can accordingly be connected to multiple conduction elements 8 and/or multiple treatment zones 4.

The example embodiments show possible variations of the method and the device for treating food and/or containers; let it be noted at this juncture that the invention is not limited to the specially portrayed variations of embodiments themselves, but that diverse combinations of the individual variations of embodiments are possible and that this possibility of variation falls within the competence of a person active in this technical field based on the teaching regarding technical action provided by this invention.

Furthermore, individual characteristics or combinations of characteristics from the depicted and described various example embodiments can constitute independent inventive or invented solutions.

The aim underlying the independent invented solutions can be taken from the description.

All information regarding ranges of values in this description should be understood to mean that these include any and all partial ranges, e.g. the statement 1 to 10 should be understood to mean that all partial ranges starting from the lower threshold 1 and the upper threshold 10 are included, i.e. all partial ranges begin with a lower threshold of 1 or larger and with an upper threshold of 10 or less, e.g. 1 to 1.7 or 3.2 to 8.1 or 5.5 to 10.

Above all, the individual embodiments shown in FIGS. 1 to 11 can form the subject of independent invented solutions. The relevant aims according to the invention and solutions can be found in the detailed descriptions of these figures.

As a matter of form, let it be noted that, to facilitate a better understanding of the design of the device for treating food and/or containers, these and their components have in places been portrayed not to scale and/or enlarged and/or scaled-down.

| List of reference signs | |
|---|---|
| 1 | Device |
| 2 | Container |
| 3 | Process liquid |
| 4 | Treatment zone |
| 5 | Liquid stream |
| 6 | Outside |
| 7 | Spray nozzle |
| 8 | Conduction element |
| 9 | Collecting tub |
| 10 | Means of transport |
| 11 | Conveying means |
| 12 | Heating means |
| 13 | Cooling means |
| 14 | Liquid tank |
| 15 | Liquid tank |
| 16 | Emptying device |
| 17 | Feeding device |
| 18 | Flow regulator apparatus |
| 19 | Membrane filtration system |
| 20 | Stream |
| 21 | Splitting means |
| 22 | Feeding element |
| 23 | Three-way splitting valve |
| 24 | Draining element |
| 25 | Opening |
| 26 | Direction of transport |
| 27 | Fan |
| 28 | Inside |
| 29 | Three-way valve |
| 30 | Pressure vessel |
| 31 | Filter membrane module |
| 32 | Receiving container |
| 33 | Filtrate |
| 34 | Closure |
| 35 | Backflush piping |
| 36 | Direction |
| 37 | Liquid waste line |
| 38 | Dispensing device |
| 39 | Chemical source |
| 40 | Adsorption device |
| 41 | Sensor |
| 42 | Switching means |
| 43 | Mixing means |
| 44 | Switching means |

-continued

| List of reference signs | |
|---|---|
| 45 | Splitting means |
| 46 | Stream |
| 47 | Flow container |

The invention claimed is:

1. A method for treating food in a plurality of treatment zones of a device for treating food, the method comprising
filling the food to be treated into containers and then closing the containers; and
transporting the closed containers through the plurality of treatment zones of the device for treating food;
feeding a process liquid into each treatment zone of the plurality of treatment zones to act on the closed containers, wherein the process liquid flows around an outside of the closed containers;
treating the food in each treatment zone of the plurality of treatment zones by heat transfer via the process liquid;
pasteurizing the food in at least one treatment zone of the plurality of treatment zones by heat transfer into the food by the process liquid;
draining the process liquid out of each treatment zone of the plurality of treatment zones after the treating of the food has been completed and then recirculating the process liquid back into each of the treatment zones of the plurality of treatment zones;
wherein during the recirculating, conducting the process liquid into piping and using at least one adjustable splitter or multiple splitters working together to form at least one stream of the process liquid by removing a partial quantity of the process liquid already present within the piping out of the piping;
wherein the at least one stream of the process liquid is filtered by at least one membrane filtration system in order to clean the at least one stream of the process liquid;
wherein after the filtration process a filtered stream is at least partially fed back into an element containing and/or conducting the process liquid and/or into a treatment zone of the plurality of treatment zones; and
wherein the treating is continuous and during the continuous treating a total volume of the process liquid contained in the device for treating food is conducted through the at least one membrane filtration system and filtered between 2 times and 10 times per day.

2. The method according to claim 1, wherein the process liquid comprises a plurality of liquid streams, and wherein each of the liquid streams of the plurality of liquid streams has a temperature set separately for each treatment zone of the plurality of treatment zones in a controlled way before each of the liquid streams of the plurality of liquid streams are fed into each of the treatment zones of the plurality of treatment zones.

3. The method according to claim 1, wherein the treating of the food comprises successively heating the food in a first treatment zone of the plurality of treatment zones, wherein the pasteurizing of the food is in a second treatment zone of the plurality of treatment zones, and the food is cooled in a third treatment zone of the plurality of treatment zones.

4. The method according to claim 3, wherein a liquid stream of the process liquid is fed into the first treatment zone for heating the closed containers at a temperature between 40° C. and 50° C.

5. The method according to claim 1, wherein the partial quantity is chosen in such a way that the filtration of the at least one stream allows for a removal rate of micro-organisms within a time interval to be achieved that is larger than a growth rate of the micro-organisms in the process liquid during the time interval.

6. The method according to claim 1, wherein the partial quantity is selected in such a way that, based on the total volume of process liquid conducted through all treatment zones of the plurality of treatment zones per time unit, at least 1% and less than 25% is used to form the at least one stream of the process liquid.

7. The method according to claim 1, wherein the partial quantity of the process liquid has a temperature of less than 80° C.

8. The method according to claim 3, wherein the process liquid used to form the at least one stream of the process liquid to be filtered has a temperature between 40° C. and 50° C.

9. The method according to claim 1, wherein the filtered stream is at least partially fed back under at least approximately ambient pressure in free fall.

10. The method according to claim 1,
wherein the plurality of treatment zones are arranged in a treatment zone line; and
wherein the filtered stream of the process liquid is at least partially fed into a treatment zone of the plurality of treatment zones for rinsing the outside of the closed containers filled with food, placed at an end of the treatment zone line.

11. The method according to claim 1,
wherein the plurality of treatment zones are arranged in a treatment zone line; and
wherein the filtered stream of the process liquid is at least partially fed into a treatment zone of the plurality of treatment zones placed at a start of the treatment zone line, for cleaning the inside and the outside of the containers before the filling.

12. The method according to claim 1, wherein the process liquid is conducted into a receiving container after the filtering by the at least one membrane filtration system and recirculated into at least one element holding and/or conducting the process liquid and/or into at least one treatment zone of the plurality of treatment zones via an overflow arranged on the receiving container.

13. The method according to claim 12, wherein the at least one membrane filtration system is operatively separated from the device for treating food at specifiable time intervals in order to clean filter membranes during ongoing operation and filtrate of the process liquid collected in the receiving container is conducted through the at least one membrane filtration system by reversing the flow direction through the filter membranes in comparison to filtration mode.

14. The method according to claim 13, wherein liquid waste accrued during cleaning by reversal of the flow direction through the filter membranes of the at least one membrane filtration system is drained and replaced by an equivalent quantity of fresh process liquid.

15. The method according to claim 1, wherein chemicals from one or more chemical sources are admixed into the at least one stream of the process liquid to be filtered and/or the filtered stream of the process liquid by a dispensing device as needed both during the treating and the filtering and additionally for cleaning the at least one membrane filtration system.

16. The method according to claim 1, wherein a degree of contamination is continuously monitored using sensors in conduction elements of a treatment zone of the plurality of treatment zones.

17. The method according to claim 1, wherein the at least one membrane filtration system comprises more than one membrane filtration system and the more than one membrane filtration system is assigned to a treatment zone of the plurality of treatment zones.

18. The method according to claim 1, wherein the process liquid is heated via a heater.

* * * * *